(12) United States Patent
Schmidt et al.

(10) Patent No.: US 7,386,199 B2
(45) Date of Patent: Jun. 10, 2008

(54) PROVIDING LIGHT TO CHANNELS OR PORTIONS

(75) Inventors: Oliver Schmidt, Palo Alto, CA (US); Setu Mohta, Haryana (IN); Peter Kiesel, Palo Alto, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 0 days.

(21) Appl. No.: 11/316,660

(22) Filed: Dec. 22, 2005

(65) Prior Publication Data

US 2007/0147728 A1  Jun. 28, 2007

(51) Int. Cl.
*G02B 6/12* (2006.01)
(52) U.S. Cl. .................................................. 385/14
(58) Field of Classification Search ............... 385/14, 385/129–132; 356/317
See application file for complete search history.

(56) References Cited

U.S. PATENT DOCUMENTS

| | | | |
|---|---|---|---|
| 2,708,389 A | 5/1955 | Kavanagh | |
| 3,797,911 A * | 3/1974 | Kogelnik et al. | 385/31 |
| 3,973,118 A | 8/1976 | LaMontagne | |
| 4,081,277 A | 3/1978 | Brault et al. | |
| 4,514,257 A | 4/1985 | Karlsson et al. | |
| 4,573,796 A | 3/1986 | Martin et al. | |
| 4,715,672 A * | 12/1987 | Duguay et al. | 385/129 |
| 4,764,670 A | 8/1988 | Pace et al. | |
| 4,957,371 A | 9/1990 | Pellicori et al. | |
| 4,976,542 A | 12/1990 | Smith | |
| 5,080,462 A | 1/1992 | Goto | |
| 5,144,498 A | 9/1992 | Vincent | |
| 5,166,755 A | 11/1992 | Gat | |

(Continued)

FOREIGN PATENT DOCUMENTS

EP  0679881 A1  11/1995

(Continued)

OTHER PUBLICATIONS

Singh et al., "Analysis of cellular structure by light scattering measurements in a new bytometer design based on a liquid-core waveguide," Feb. 5, 2004, IEEE Proceedings, vol. 151, Issue 1, pp. 10-16.*

(Continued)

*Primary Examiner*—M. R. Connelly-Cushwa
*Assistant Examiner*—Kajli Prince
(74) *Attorney, Agent, or Firm*—James T. Beran; Leading-Edge Law Group, PLC

(57) ABSTRACT

A fluidic structure includes a channel, a portion of which can contain fluid. Light can propagate in the portion, such as in response to illumination. The refractive index of material at the portion's boundary can be higher than that of the fluid, and more than approximately 10% of intensity of light propagating longitudinally occurs in the fluid, possibly approximately 90%. An IC can be positioned along the portion, with a set of cells of a photosensor array on the IC sensing photons emanating in response to the propagating light. The light can enter through a light-transmissive component along the channel's boundary, then pass obliquely through a portion of the channel that contains air before passing through a bounding component and obliquely into the portion that can contain fluid. The light can couple to an anti-resonant waveguide mode.

35 Claims, 11 Drawing Sheets

U.S. PATENT DOCUMENTS

| | | |
|---|---|---|
| 5,305,082 A | 4/1994 | Bret |
| 5,324,401 A * | 6/1994 | Yeung et al. ............... 204/452 |
| 5,370,842 A | 12/1994 | Miyazaki et al. |
| 5,572,328 A * | 11/1996 | Fouckhardt et al. ........ 356/440 |
| 5,682,038 A | 10/1997 | Hoffman |
| 5,777,329 A | 7/1998 | Westphal et al. |
| 5,784,507 A | 7/1998 | Holm-Kennedy et al. |
| 5,792,663 A | 8/1998 | Fry et al. |
| 5,801,831 A | 9/1998 | Sargoytchev |
| 5,864,641 A | 1/1999 | Murphy et al. |
| 5,876,674 A | 3/1999 | Dosoretz et al. |
| 5,880,474 A | 3/1999 | Norton et al. |
| 6,108,463 A * | 8/2000 | Herron et al. ............... 385/12 |
| 6,137,117 A | 10/2000 | Feldstein et al. |
| 6,192,168 B1 | 2/2001 | Feldstein et al. |
| 6,216,022 B1 | 4/2001 | Tyrrell et al. |
| 6,249,346 B1 | 6/2001 | Chen et al. |
| 6,275,628 B1 | 8/2001 | Jones et al. |
| 6,295,130 B1 | 9/2001 | Sun et al. |
| 6,353,475 B1 | 3/2002 | Jensen et al. |
| 6,399,405 B1 | 6/2002 | Chen et al. |
| 6,405,073 B1 | 6/2002 | Crowley et al. |
| 6,429,022 B1 | 8/2002 | Kunz et al. |
| 6,459,080 B1 | 10/2002 | Yin et al. |
| 6,483,959 B1 * | 11/2002 | Singh et al. ................. 385/12 |
| 6,490,034 B1 | 12/2002 | Woias et al. |
| 6,505,775 B1 | 1/2003 | Gu et al. |
| 6,519,037 B2 | 2/2003 | Jung et al. |
| 6,525,308 B1 | 2/2003 | Schmidt-Hattenberger |
| 6,558,945 B1 | 5/2003 | Kao |
| 6,577,780 B2 | 6/2003 | Lockhart |
| 6,580,507 B2 | 6/2003 | Fry et al. |
| 6,603,548 B2 | 8/2003 | Church et al. |
| 6,608,679 B1 | 8/2003 | Chen et al. |
| 6,630,999 B2 | 10/2003 | Shroder |
| 6,785,002 B2 | 8/2004 | Zarrabian et al. |
| 6,800,849 B2 | 10/2004 | Staats |
| 6,867,420 B2 | 3/2005 | Mathies et al. |
| 6,870,149 B2 | 3/2005 | Berezin |
| 6,887,713 B2 | 5/2005 | Nelson et al. |
| 7,064,836 B2 | 6/2006 | Bechtel et al. |
| 7,149,396 B2 | 12/2006 | Schmidt et al. |
| 7,248,361 B2 | 7/2007 | Kiesel et al. |
| 7,268,868 B2 | 9/2007 | Kiesel et al. |
| 7,291,824 B2 | 11/2007 | Kiesel et al. |
| 7,310,153 B2 | 12/2007 | Kiesel et al. |
| 7,315,667 B2 | 1/2008 | Schmidt et al. |
| 2002/0155485 A1 | 10/2002 | Kao |
| 2003/0000835 A1 | 1/2003 | Witt et al. |
| 2003/0020915 A1 | 1/2003 | Schueller et al. |
| 2003/0077660 A1 | 4/2003 | Pien et al. |
| 2003/0235924 A1 | 12/2003 | Adams et al. |
| 2004/0027462 A1 | 2/2004 | Hing |
| 2004/0031684 A1 | 2/2004 | Witt |
| 2004/0032584 A1 | 2/2004 | Honda et al. |
| 2004/0038386 A1 | 2/2004 | Zesch et al. |
| 2004/0067167 A1 | 4/2004 | Zhang et al. |
| 2004/0132214 A1 | 7/2004 | Lin et al. |
| 2004/0141884 A1 | 7/2004 | Unno et al. |
| 2004/0145738 A1 | 7/2004 | Sun et al. |
| 2004/0175734 A1 | 9/2004 | Stahler et al. |
| 2004/0223881 A1 | 11/2004 | Cunningham et al. |
| 2004/0252957 A1 | 12/2004 | Schmidt et al. |
| 2005/0042615 A1 | 2/2005 | Smith et al. |
| 2005/0068526 A1 | 3/2005 | Avrutsky |
| 2005/0084203 A1 | 4/2005 | Kane |
| 2005/0128479 A1 | 6/2005 | Gilbert et al. |
| 2006/0039009 A1 | 2/2006 | Kiesel et al. |
| 2006/0046312 A1 | 3/2006 | Kiesel et al. |
| 2006/0092413 A1 * | 5/2006 | Kiesel et al. ............... 356/301 |
| 2006/0121555 A1 | 6/2006 | Lean et al. |
| 2006/0193550 A1 | 8/2006 | Wawro et al. |
| 2006/0274313 A1 | 12/2006 | Gilbert et al. |
| 2007/0070347 A1 | 3/2007 | Scherer et al. |
| 2007/0116609 A1 | 5/2007 | Baeuerle et al. |
| 2007/0145236 A1 | 6/2007 | Kiesel et al. |
| 2007/0145249 A1 | 6/2007 | Kiesel et al. |
| 2007/0146704 A1 | 6/2007 | Schmidt et al. |
| 2007/0146888 A1 | 6/2007 | Schmidt et al. |
| 2007/0147189 A1 | 6/2007 | Schmidt et al. |
| 2007/0147726 A1 | 6/2007 | Kiesel et al. |
| 2007/0148760 A1 | 6/2007 | Kiesel et al. |

FOREIGN PATENT DOCUMENTS

| | | |
|---|---|---|
| EP | 1801564 A1 | 6/2007 |
| WO | WO 95/20144 | 7/1995 |
| WO | WO 99/44042 A2 | 9/1999 |
| WO | WO 00/62050 | 10/2000 |
| WO | WO 02/25269 A2 | 3/2002 |

OTHER PUBLICATIONS

Bernini et al., "Silicon Micromachined Hollow Optical Waveguides for Sensing Applications," Jan.-Feb. 2002, vol. 8, Issue 1, pp. 106-110.*

"Developing technology: HPLC-Chip/MS", Agilent Technologies, printed from www.chem.agilent.com on Aug. 2, 2005, 2 pages.

Singh, K., and Goddard, N.J., "Leaky ARROW Waveguides for Optical Chemical and Biosensors", (Abstract Submitted to Biosensors 1998), printed from dias.umist.ac.uk on Aug. 1, 2005, 2 pages.

"Abstracts of Published Work", printed from dias.umist.ac.uk on Aug. 1, 2005, 3 pages.

Goddard, N.J., Singh, K., Bounaira, F., Holmes, R.J., Baldock, S.J., Pickering, L.W., Fielden, P.R., and Snook, R.D., "Anti-Resonant Reflecting Optical Waveguides (ARROW), as Optimal Optical Detectors for Micro TAS Applications", printed from dias.umist. ac.uk on Aug. 1, 2005, pp. 1-5.

Sivaprakasam, V., Huston, A., Eversole, J., and Scotto, C., Multiple UV Wavelength Excitation and Fluorescence of Bioaerosols, 2nd Joint Conference on Point Detection, Williamsburg, VA, 2004, 10 pages.

Koch, M., Evans, A.G.R., and Brunnschweiler, A., "Design and fabrication of a micromachined Coulter counter", J. Micromech. Microeng. 9, 1999, pp. 159-161.

Agilant Technologies, "Agilent 83453B High-Resolution Spectrometer—Technical Specifications", Feb. 2005, pp. 1-8.

Liu, G.L., and Lee, L.P., "Nanowell surface enhanced Raman scattering arrays fabricated by soft-lithography for label-free biomolecular detections in integrated microfluidics", Applied Physics Letters, vol. 87, 2005, pp. 1-3.

Devasenathipathy, S., and Santiago, J.G., "3 Electrokinetic Flow Diagnostics" in Breuer, K.S., Ed., Micro-and Nano-Scale Diagnostic Techniques, Springer Verlag, New York, 2003, pp. 121-166.

Becker, H., and Gartner, C., "Polymer microfabrication methods for microfluidic analytical applications", Electrophoresis, vol. 21, 2000, pp. 12-26.

Jones, T.B., Gunji, M., Washizu, M., and Feldman, M.J., "Dielectrophoretic liquid actuation and nanodroplet formation", Journal of Applied Physics, vol. 89, No. 2, 2001, pp. 1441-1448.

Adams, M.L., Enzelberger, M., Quake, S., and Scherer, A., "Microfluidic integration on detector arrays for absorption and fluorescence micro-spectrometers,"Sensors and Actuators A, vol. 104, 2003, pp. 25-31.

European Search Report and Annex for Counterpart EPO Application No. EP 06 12 6528, dated Mar. 29, 2007, 6 pages.

Communication from European Patent Office including extended European Search Report with European Search Report and Annex and European search opinion for counterpart EPO Application No. EPO 6126528, dated Apr. 5, 2007, 7 pages.

Office communication in U.S. Appl. No. 10/922,870, mailed Jul. 26, 2007, 11 pages, published on PAIR.

Office communication in U.S. Appl. No. 10/922,870, mailed Sep. 24, 2007, 3 pages, published on PAIR.

Amendment in U.S. Appl. No. 10/922,870, dated Apr. 30, 2007, 15 pages, published in PAIR.

Amendment in U.S. Appl. No. 10/922,870, dated Sep. 14, 2007, 9 pages, published in PAIR.

Amendment in U.S. Appl. No. 10/922,870, dated Oct. 4, 2007, 9 pages, published in PAIR.

Notice of Allowance and Fee(s) Due and attached papers for U.S. Appl. No. 11/315,387, mailed Jun. 20, 2007, 23 pages, published in PAIR.

Notice of Allowance and Fee(s) Due and attached papers for U.S. Appl. No. 11/315,387, mailed Oct. 5, 2007, 7 pages, published in PAIR.

Amendment with Request for Continued Examination in U.S. Appl. No. 11/315,387, dated Sep. 18, 2007, 6 pages, published in PAIR.

Notice of Allowance and Fee(s) due and attached papers for U.S. Appl. No. 11/316,438, mailed Jul. 6, 2007, 20 pages, published in PAIR.

Notice of Allowance and Fee(s) due and attached papers for U.S. Appl. No. 11/315,992, mailed Oct. 3, 2007, 19 pages, published in PAIR.

Notice of Allowance and Fee(s) due and attached papers for U.S. Appl. No. 10/922,870, mailed Oct. 22, 2007, 7 pages, published in PAIR.

Office communication in U.S. Appl. No. 11/315,926, mailed Dec. 28, 2007, 17 pages, published in PAIR.

\* cited by examiner

FIG. 2
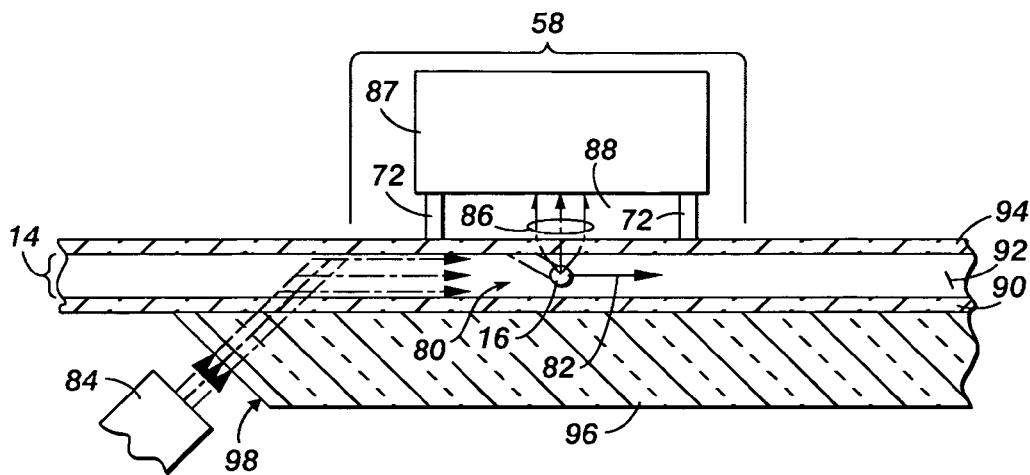
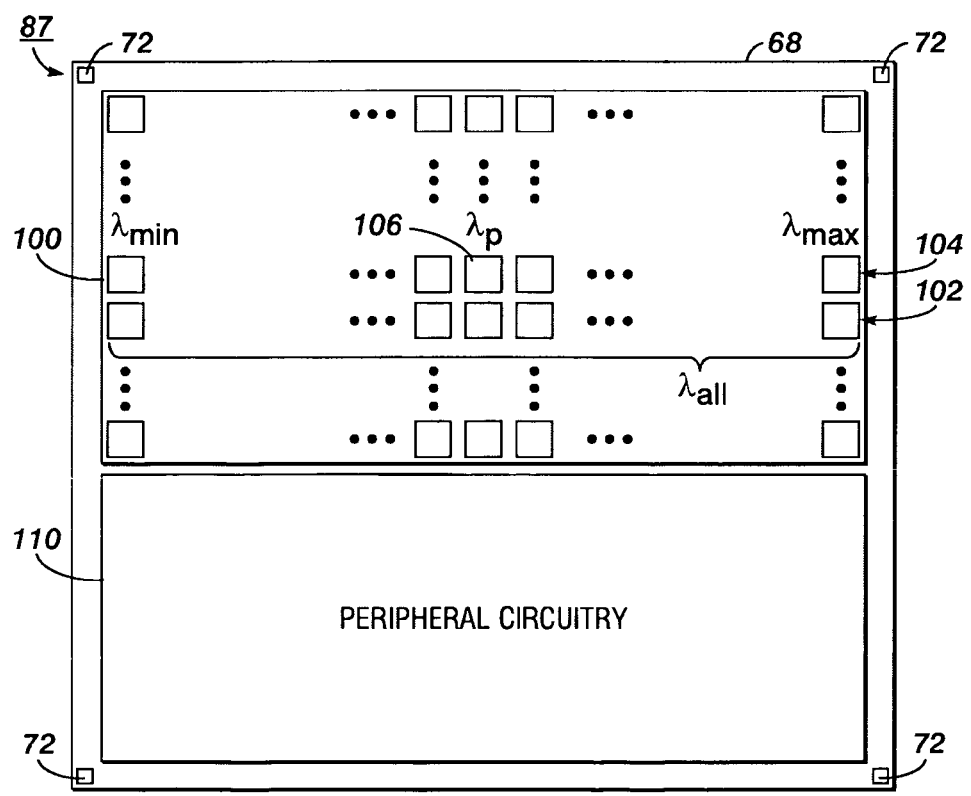
FIG. 3

FIG. 15
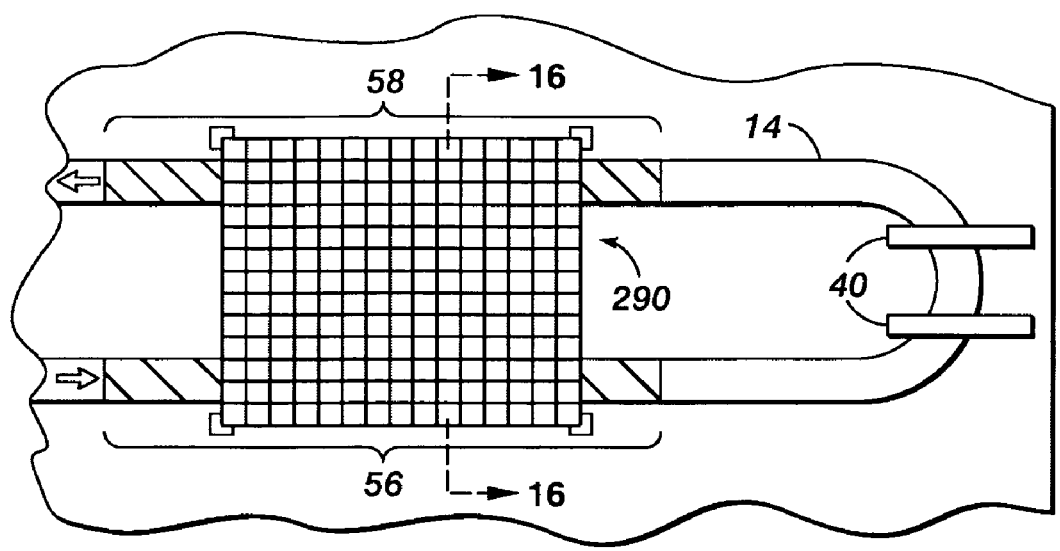
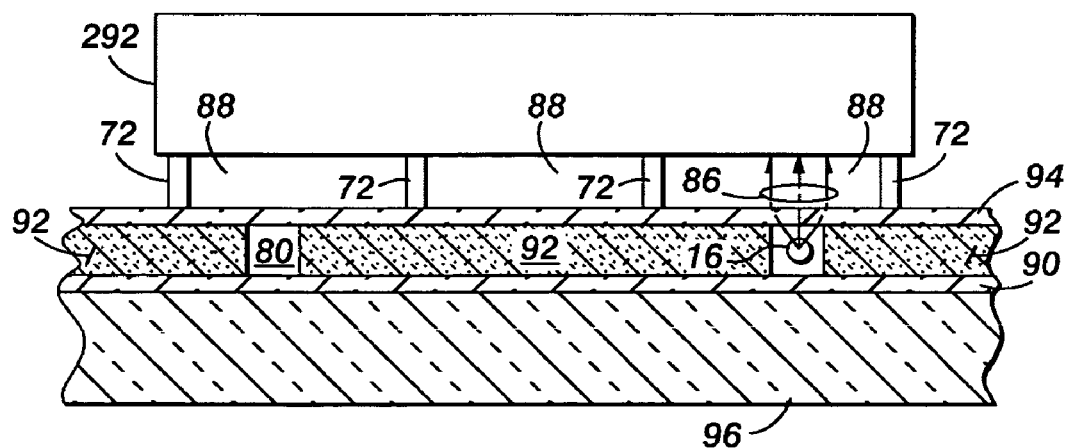
FIG. 16

PROVIDING LIGHT TO CHANNELS OR PORTIONS

The present application is related to the following co-pending applications, each of which is hereby incorporated by reference in its entirety: "Anti-resonant Waveguide Sensors", U.S. patent application Ser. No. 10/976,434, now published as U.S. Patent Application Publication No. 2006/0092413 and issued as U.S. Pat. No. 7,268,868; "Bio-Enrichment Device to Enhance Sample Collection and Detection", U.S. patent application Ser. No. 11/007,121, now published as U.S. Patent Application Publication No. 2006/0121555; "Photosensing Throughout Energy Range and in Subranges", U.S. patent application Ser. No. 11/316,438, now issued as U.S. Pat. No. 7,291,824; "Sensing Photon Energies of Optical Signals", U.S. patent application Ser. No. 11/315,926; "Sensing Photons From Objects in Channels", U.S. patent application Ser. No. 11/315,992; "Sensing Photon Energies Emanating from Channels or Moving Objects", U.S. patent application Ser. No. 11/315,386; "Transmitting Light With Photon Energy Information", U.S. patent application Ser. No. 11/316,241; "Obtaining Analyte Information", U.S. patent application Ser. No. 11/316,303; and "Propagating Light to be Sensed", U.S. patent application Ser. No. 11/315,387, now issued as U.S. Pat. No. 7,315,667.

BACKGROUND OF THE INVENTION

The present invention relates generally to providing light to channels or portions of channels, such as in applications in which photons emanate from the channels or portions in response to propagating light.

Goddard, N. J., Singh, K., Bounaira, F., Holmes, R. J., Baldock, S. J., Pickering, L. W., Fielden, P. R., and Snook, R. D., "Anti-Resonant Reflecting Optical Waveguides (AR-ROWs) as Optimal Optical Detectors for MicroTAS Applications", dias.umist.ac.uk/NJG/Abstracts/MicroTAS/MicroTas2.htm, pp. 1-5, describe techniques in which light is confined in a low refractive index medium, such as an aqueous solution, surrounded by high refractive index reflecting boundaries, such as highly reflective Fabry-Perot resonators. Optical detection can be performed via an evanescent field at the channel-waveguide boundary, or a CCD chip can be instead used to monitor angle changes.

U.S. Pat. No. 6,580,507 describes a multiple-longitudinal flow cell channel system in which an array detector is positioned to monitor radiation from at least two of multiple flow cell channels, at separate groupings of pixels on the detector. Absorption or fluorescence of analytes in response to electromagnetic radiation can be monitored, where the analytes are contained in fluid flowing through the channels.

It would be advantageous to have improved techniques for providing light to channels or portions of channels.

SUMMARY OF THE INVENTION

The invention provides various exemplary embodiments, including methods, apparatus, and systems. In general, the embodiments are implemented with light provided to channels or portions of channels in fluidity structures.

These and other features and advantages of exemplary embodiments of the invention are described below with reference to the accompanying drawings.

BRIEF DESCRIPTION OF THE DRAWINGS

FIG. 2 is a schematic cross-sectional view of the analyzer in FIG. 1, taken along the line 2-2.

FIG. 3 is a schematic plan view of an implementation of an assembly that can be used in FIG. 2, including an integrated circuit (IC) with a photosensor array.

FIG. 15 is a schematic drawing of an alternative implementation of part of an analyzer on a fluidity structure as in FIG. 1.

FIG. 16 is a schematic cross-sectional view of the alternative implementation in FIG. 15, taken along the line 16-16.

DETAILED DESCRIPTION

Figure 1:
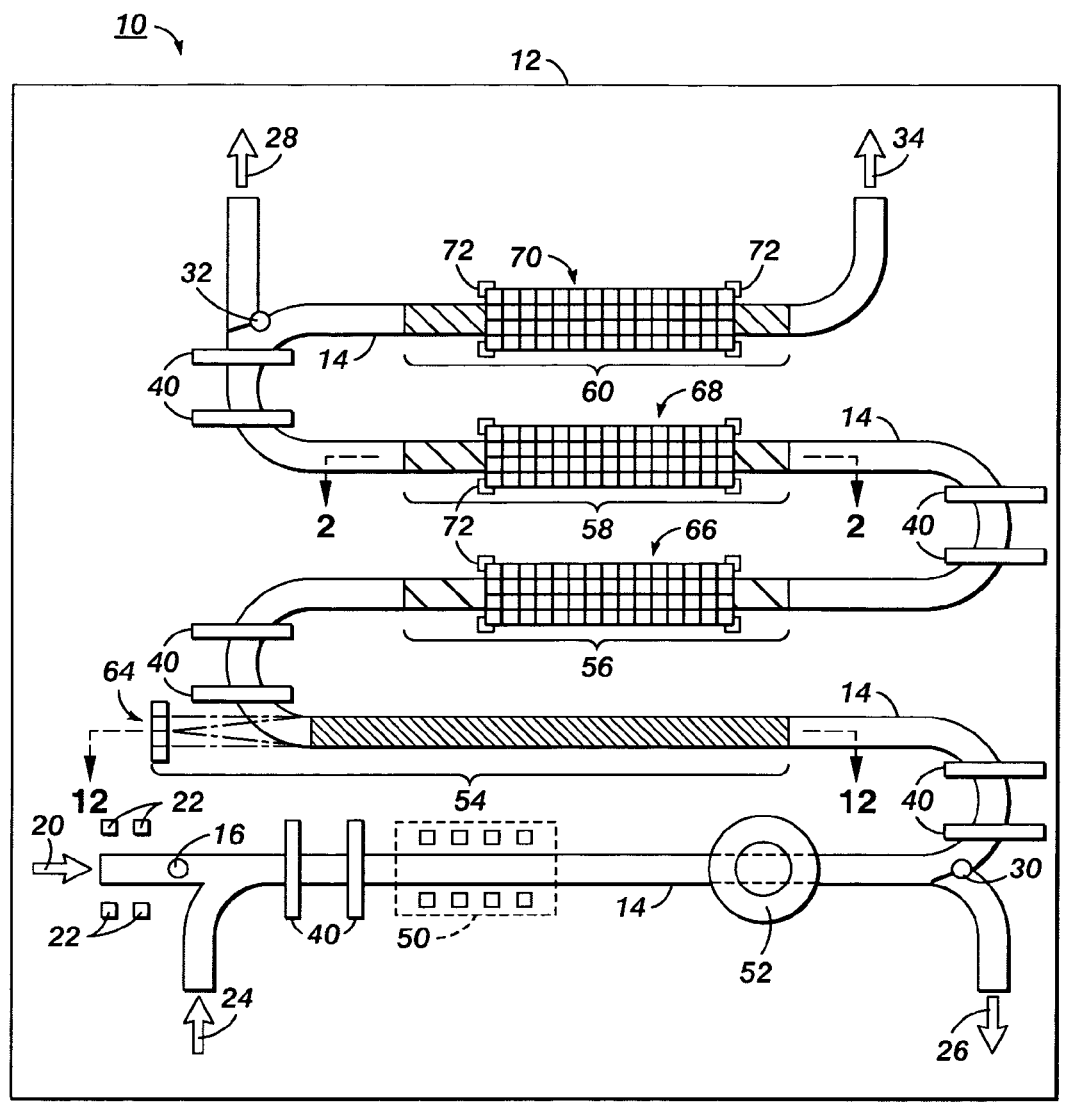
FIG. 1 is a schematic diagram of an analyzer on a fluidity structure.

In the following detailed description, numeric values and ranges are provided for various aspects of the implementations described. These values and ranges are to be treated as examples only, and are not intended to limit the scope of the claims. In addition, a number of materials are identified as suitable for various facets of the implementations. These materials are to be treated as exemplary, and are not intended to limit the scope of the claims.

"Light" refers herein to electromagnetic radiation of any wavelength or frequency; unless otherwise indicated, a specific value for light wavelength or frequency is that of light propagating through vacuum. The term "photon" refers herein to a quantum of light, and the term "photon energy" refers herein to the energy of a photon.

To "propagate" light through a region or structure is to transmit or otherwise cause the light to propagate through the region or structure. The light may be referred to as "propagated light" or "propagating light".

The various exemplary implementations described below address problems that arise in propagating light in certain contexts. In particular, the implementations address problems that arise in efficiently and effectively illuminating objects, especially in situations in which photons emanate from objects in response to propagating light and in situations in which many objects are far apart from each other and all of them should be illuminated, such as for large area excitation. The emanating photons can be sensed, such as to determine characteristics of analytes within the waveguide.

These problems can arise for biosensors that use light to investigate analytes of interest. The interaction between light and analyte is typically very weak. To improve the interaction, optical waveguides can be used, but usually the fluid or other substance that contains the analyte cannot itself be used as an optical waveguide, because its refractive index is lower than the index of surrounding material. Therefore, a conventional optical waveguide typically provides only weak interaction with target molecules, through evanescent waves along the periphery of the waveguide.

The term "sensing" is used herein in the most generic sense of obtaining information from a physical stimulus; sensing therefore includes actions such as detecting, measuring, and so forth. A "sensing component" is any component that performs sensing.

To "photosense" is to sense photons, and to "photosense quantity" of photons is to obtain information indicating a quantity of the photons. Photons that are photosensed are sometimes referred to herein as "incident photons".

A "photosensor" is used herein to refer generally to any element or combination of elements that senses photons, whether by photosensing quantity or any other information about the photons. A photosensor could, for example, provide an electrical signal or other signal that indicates sensed information, such as a signal indicating quantity of incident photons.

Some of the photosensing implementations described herein employ structures with one or more dimensions smaller than 1 mm, and various techniques have been proposed for producing such structures. In particular, some techniques for producing such structures are referred to as "microfabrication." Examples of microfabrication include various techniques for depositing materials such as growth of epitaxial material, sputter deposition, evaporation techniques, plating techniques, spin coating, printing, and other such techniques; techniques for patterning materials, such as etching or otherwise removing exposed regions of thin films through a photolithographically patterned resist layer or other patterned layer; techniques for polishing, planarizing, or otherwise modifying exposed surfaces of materials; and so forth.

In general, the structures, elements, and components described herein are supported on a "support structure" or "support surface", which terms are used herein to mean a structure or a structure's surface that can support other structures. More specifically, a support structure could be a "substrate", used herein to mean a support structure on a surface of which other structures can be formed or attached by microfabrication or similar processes.

The surface of a substrate or other support surface is treated herein as providing a directional orientation as follows: A direction away from the surface is "up", "over", or "above", while a direction toward the surface is "down", "under", or "below". The terms "upper" and "top" are typically applied to structures, components, or surfaces disposed away from the surface, while "lower" or "underlying" are applied to structures, components, or surfaces disposed toward the surface. In general, it should be understood that the above directional orientation is arbitrary and only for ease of description, and that a support structure or substrate may have any appropriate orientation.

An "integrated circuit" or "IC" is a structure with electrical components and connections produced by microfabrication or similar processes. An IC may, for example, be on or over a substrate on which it was produced or another suitable support structure. Other components could be on the same support structure with an IC, such as discrete components produced by other types of processes.

Implementations described herein include features characterized as "cells" and "arrays", terms that are used with related meanings: An "array" is an arrangement of "cells". An array on an IC or other support structure may also include circuitry that connects to electrical components within the cells such as to select cells or transfer signals to or from cells, and such circuitry is sometimes referred to herein as "array circuitry". In contrast, the term "peripheral circuitry" is used herein to refer to circuitry on the same support surface as an array and connected to its array circuitry but outside the array. The term "external circuitry" is more general, including not only peripheral circuitry but also any other circuitry that is outside a given cell or array.

A "photosensor array" is an array in which some or all of the cells are or include photosensors. Accordingly, an IC "includes" a photosensor array if the IC includes an array of cells, and at least some of the cells include respective photosensors.

In an application that includes a photosensor array, circuitry that "responds to" the photosensor array can be any circuitry that, in operation, receives information from the photosensor array about its photosensing results through an electrical connection. Circuitry that responds to a photosensor array could be circuitry in the photosensor array, or it could be peripheral circuitry or other external circuitry, or it could include any suitable combination of array circuitry, peripheral circuitry, and other external circuitry.

FIG. 1 shows schematically some components of analyzer 10 on support structure 12, a fluidity structure. Defined in support structure 12 is serpentine channel 14 through which an object 16 can travel, carried by a fluid or other appropriate substance. Object 16 can, for example, be a droplet or small volume of fluid that includes an analyte to be analyzed.

The term "object" is used herein in the general sense of any distinguishable thing from which light can emanate, whether through emission (e.g. radiation, fluorescence, incandescence, luminescence, etc.), scattering (e.g. reflection, deflection, diffraction, refraction, etc.), or transmission. The light "emanates from" or is simply "from" the object.

Examples of objects that could occur in implementations as described below include droplets, small volumes of fluid, single molecules, agglomerated molecules, molecule clusters, cells, viruses, bacteria, proteins, DNA, microparticles, nanoparticles, and emulsions. A droplet or small volume of fluid may, for example, include atoms, molecules, or other particles that emit light spontaneously or in response to excitation; a particle could be a "fluorescent component" of a droplet, fluorescing in response to excitation. Or a droplet may include particles that absorb light incident on the droplet, so that the droplet does not reflect or otherwise scatter the absorbed light; in this case, a particle could be an "absorbent component" of a droplet. Or a droplet may include particles that scatter light incident on the droplet in a way that depends on photon energy, so that the droplet scatters the incident light correspondingly; in this case, a particle could be an "scattering component" of a droplet. An analyte (i.e. a chemical species being investigated) in a droplet can act as a fluorescent, absorbent, or scattering component.

An object "travels" or is caused "to travel" if the object moves through a succession of positions. For example, the object could be conveyed in a fluid, such as a liquid, gas, or aerosol, in which case the object may be referred to as being "carried" by the fluid.

Some exemplary implementations of the invention involve fluidity techniques; as noted above, the term "fluid" is used herein to encompass liquids, gasses, and aerosols. The terms "fluidity structure" and "channel" are used herein with related meanings: A "fluidity structure" is a structure that depends for its operation on fluid positioning or fluid flow, such as, for liquids or gases, in response to pressure or, for liquids, as a result of surface tension effects; a "channel" is any tube or other enclosed passage within a fluidity structure through which fluid flows during operation.

A channel or portion of a channel is treated herein as providing a directional orientation as follows: A "cross section" lies in a plane perpendicular to a direction in which a local net flow of fluid through the channel or portion can occur; a direction in which a cross section extends can be referred to as a "transverse direction". "Longitudinal direction" is direction perpendicular to a cross section of a channel or portion; since longitudinal direction can differ for different cross sections, longitudinal direction may not be linear, but could include one or more curves or bends. Similarly, "length" of a channel or portion Is measured in its longitudinal direction, and the term "lengthwise" similarly refers to motion or extent in a longitudinal direction of a channel or portion. Relative to a longitudinal direction, an "oblique direction" is a direction that is neither parallel to nor perpendicular to the longitudinal direction. A channel or portion with approximately uniform cross section and substantially linear longitudinal direction can be referred to as "straight", and the channels and portions described herein are generally straight unless otherwise indicated.

A "boundary" of a channel or portion is the surface within which fluid contained in the channel is confined. A "port" is an opening that extends through the boundary of a channel or portion such that fluid can enter or exit through the port; in general, a port is relatively small compared to the channel or portion, and the boundary is treated as extending across the port as if the port did not exist. In a given cross section of a channel or portion, it may therefore be "surrounded" along most of its boundary by material, meaning that more than half of its boundary in the cross section is bounded by material rather than being a port or ports.

An object "travels" within a channel or a portion of a channel or is caused "to travel" within a channel or a portion if the object moves through a succession of positions in the channel or portion. Similarly, light "emanates" from a channel or a portion of a channel if the light emanates from one or more objects within the channel or portion, where the term "object" is broadly understood to include even single molecules and small volumes of fluid from which light can emanate.

Object 16 enters channel 14 carried by a primary fluid illustrated by arrow 20, and can enter from a supply reservoir (not shown) and a sample well (not shown), with its entry into the primary fluid controlled by metering electrodes 22. The supply reservoir could, for example, be a microfabricated bio-enrichment device with a cell on which concentration occurs, as described in co-pending U.S. patent application Ser. No. 11/007,121, entitled "Bio-Enrichment Device to Enhance Sample Collection and Detection" and incorporated herein by reference in its entirety. Separated bands in the bio-enrichment sample well could be selectively directed into channel 14. Rather than electrical metering, as with electrodes 22, pressure metering could be used. Other possible techniques that could be implemented to provide a droplet or other small object to channel 14 could employ capillary forces or electro-osmotic flow pumps.

Although FIG. 1 illustratively shows an implementation with only one channel 14 receiving analyte samples from a single sample well (not shown) or other analyte container, analyte 10 could be implemented with any appropriate number of channels similar to channel 14, and with each channel receiving analyte samples from a respective sample well. Furthermore, each of the channels could have a different combination of components suitable to a specific type of analysis such as fluorescence spectroscopy, laser-induced fluorescence spectroscopy (LIF), absorption spectroscopy, excitation spectroscopy, Raman scattering, surface-enhanced Raman scattering (SERS), far-infrared spectroscopy, etc. Each sample well could continuously collect a specific analyte for stationary or post-detection schemes. The channels could be formed by subdividing a broad channel into several parallel channels.

Additional fluid to carry object 16 may enter as shown by arrow 24, such as to permit a constant flow rate or consistent flow independent of the analyte supply. The path followed by the fluid in channel 14 can be controlled through a number of devices. For example, the fluid, together with object 16 if appropriately positioned, can be purged at two outlets as illustrated by arrows 26 and 28 through toggling of valves 30 and 32, respectively, each of which is at a bifurcation junction. Rather than valves, other types of gates could be used, such as electric fields to selectively deflect objects; charged particles could be deflected by Coulomb force, and polarizable particles could be deflected by dielectrophoretic force. If the fluid is not purged by operating valves 30 and 32 or other similar valves (not shown) or by some other type of gate, it is purged at a final outlet from channel 14, illustrated by arrow 34.

The flow of the fluid can be maintained by conventional propulsion components such as electro-osmotic pumps 40 or some suitable hydraulic pressure pump appropriately positioned along the length of channel 14. A wide variety of other propulsion components could be used, including, for example, gas pressure pumps, positive displacement pumps, micro-peristaltic pumps, electro-kinetic pumps, piezo pumps, and thermal mode pumps. Various techniques for fluid propulsion are described in Devasenathipathy, S., and Santiago, J. G., "Electrokinetic Flow Diagnostics", in Breuer, K. S., Ed., *Micro and Nano-Scale Diagnostic Techniques*, Springer-Verlag, New York, 2003, pp.113-154, incorporated herein by reference. In addition to maintaining flow of fluid, propulsion components can also perform system flush and initial fluid loading functions, with pressure driven techniques. Appropriate circuitry (not shown) can coordinate the various pumps and other components to work in a synchronized manner.

Pressure driven flow creates a parabolic velocity profile due to fluid resistance at the walls of a channel, which leads to band spreading. Spreading and other forms of band distortion will also be evident in fluid passing through one of the serpentine curves in channel 14. Appropriate techniques can be used to track discrete analytes and provide flow cross section commensurate with analyte size.

Electro-osmotic flow (EOF) results from motion of ions inside the Debye layer due to an applied electric field in a channel direction. A Debye layer forms if the channel walls charge up when in contact with the solvent, e.g. water. The charged wall surface attracts oppositely charged counter ions, which concentrate in a thin layer next to the surface. The Debye layer has a thickness of $$\lambda_D = \left(\frac{\varepsilon kT}{q^2 n}\right)^{1/2},$$

where $\varepsilon$ indicates the dielectric constant, k indicates the Boltzman constant, T indicates the temperature, q indicates the ion charge, and n indicates the concentration of ions. Application of a potential difference in the direction of the channel causes the Debye layer to move with the electric field and, due to viscous drag, to create bulk fluid flow. The velocity profile is flat so that band distortion is a minimum. It should be noted, however, that EOF is dependent on wall charge, which is in turn affected by pH.

Various techniques can be used to control the flow of analytes, such as by directing them into different channels depending on their properties. This allows purging of benign or uninteresting particles, or the use of different detection schemes for different classes of particles that have been identified in initial detection steps. For example, the propulsion components can be coordinated with appropriate additional components for gating, metering, sorting, bifurcating, and otherwise logically controlling flow, such as with valves 30 and 32 and other appropriate devices controlled by switching electrodes and charge control.

Along channel 14 is a series of sensing components, each of which obtains information about object 16 as it travels within a respective straight portion of channel 14; the straight portions are separated by 180-degree curved portions, allowing a compact arrangement of several sensing components and interactive detection. Coulter counter 50 and Mie scatter sensor 52, for example, are conventional sensing components, illustratively along parts of one straight portion of channel 14. Coulter counter 50 is an example of an electrically based particle size detector, and could be implemented as described, for example, in Koch, M., Evans, A. G. R., and Brunnschweiler, A., "Design and Fabrication of a Micromachined Coulter Counter", J. Micromech. Microeng., Vol. 9, 1999, pp. 159-161, incorporated herein by reference. Mie scatter sensor 52 is an example of an optical detector that relies on particle-induced scattering of light entering from the side of channel 14.

Coulter counter 50 can be implemented to size particles in the 1-10 μm range within a continuous liquid stream. The Coulter counter technique should also work for other particle sizes as long as the inner diameter of channel 14 in the sensing region is not more than an order of magnitude larger than the particles being measured. Also, larger particles are harder to handle in microfluidic systems, i.e. fluidity systems in which channels have maximum transverse inner dimensions less than 0.1 mm; in such systems, larger particles tend to sediment if their density is greater than that of the solvent.

In Coulter counter 50, particles suspended in an electrically conducting solution can be drawn through a small aperture between two electrodes. A voltage applied across the aperture creates a sensing zone, and each particle passing through the sensing zone displaces its own volume of conducting liquid. The particle has infinite resistance, even if itself conductive, because polarization effects at the particle-electrolyte interface prevent any current from flowing through the particle itself. Therefore, the particle's resistance causes a momentary increase of impedance across the aperture. This change in impedance produces a tiny current flow that can be received by an amplifier and converted into a voltage pulse large enough for accurate measurement.

The Coulter principle states that the amplitude of this pulse is directly proportional to the volume of the particle, so that scaling pulse heights in volume units provides information about particle size. A size distribution can be obtained and displayed.

Mie scattering is another conventional technique for determining particle size in a free stream. Mie scattering refers to the elastic interaction of electromagnetic waves with particles having diameter at least one-tenth of the wavelength of incident light. The radiation pattern is predominantly forward scatter, with an invariant scattered angular pattern that is symmetrical along the axis of incident light for a perfect sphere. The scattered intensity increases with sphere radius, so that large particles may be distinguished from small particles by the strength of light reflected from their surfaces at a given angle. Mie scattering using light of different wavelengths has been successfully applied to size measurements of single bioaerosol particles.

The series of sensing components also includes optical (e.g. visible or infrared) absorption sensing component 54, first fluorescence sensing component 56, second fluorescence sensing component 58, and Raman scatter sensing component 60. These are merely exemplary, however, and analyzer 10 could include any other suitable combination of sensing components, including some that are not connected in series. In particular, additional sensing components (not shown) could include conventional optical or electrical trigger elements that provide a signal indicating when an analyte with properties meeting certain criteria moves past a position along channel 14. Furthermore, it may be possible to include sensing components for electrical impedance spectroscopy (EIS) for electronic pathology rather than sensing differential resistance for bioparticle sizing.

A series of sensing components as in FIG. 1 makes it possible to obtain spectral information about moving particles or other objects in order to achieve orthogonal characterization and reliable identification. Characterization is orthogonal if sensing components obtain information about orthogonal characteristics of a moving object, such as by photosensing different ranges of photon energies; sensing components could also be suitable for different intensity ranges. By choosing suitable materials, it is possible to obtain spectral information for the entire range from the deep ultraviolet to the far infrared or even for frequencies in the THz range.

Analyzer 10 can be designed to perform multi-signal analysis for a specific application, whether high wavelength resolution or broadband detection is desired. The technique illustrated in FIG. 1 also takes advantage of the motion of object 16 with a geometry that enables long integration times without sacrificing throughput capacity. Highly sensitive optical characterization methods can be used, such as fluorescence spectroscopy (illustratively in more than one range of photon energies) and Raman spectroscopy. Sivaprakasam, V., Houston, A., Scotto, C., and Eversole, J., "Multiple UV Wavelength Excitation and Fluorescence of Bioaerosols", Optics Express, Vol. 12, No. 9 (2004), pp. 4457-4466, have shown that using different UV excitation ranges provides more specific information about an analyte.

Also, the use of multi-signal analysis makes it possible to perform reagentless bioagent identification.

Each of sensing components 54, 56, 58, and 60 includes a respective one of ICs 64, 66, 68, and 70, features of which are described in greater detail below. In general, however, each of these ICs includes a photosensor array, and the sensing component includes a set of cells of the photosensor array. The set of cells photosenses photons within a range of photon energies; for example, the sets of cells in ICs 66 and 68 could photosense different ranges of photon energies in the visible to ultraviolet range, and, as noted above, the set of cells in IC 70 could photosense in the infrared. Furthermore, more than one IC, such as ICs 66 and 68, could photosense fluorescing photons that are in the same energy range, but that result from excitation at different wavelengths such as from different LED or laser light sources. As explained in co-pending U.S. patent application Ser. No. 11/316,438, entitled "Photosensing Throughout Energy Range and in Subranges"; U.S patent application Ser. No. 11/315,926, entitled "Sensing Photon Energies of Optical Signals"; U.S. patent application Ser. No. 11/315,992, entitled "Sensing Photons from Objects in Channels"; and U.S. patent application Ser. No. 11/315,386, entitled "Sensing Photon Energies Emanating from Channels or Moving Objects", all of which are incorporated herein by reference, the set of cells for each of sensing components 54, 56, 58 and 60 includes a subset of cells, each of which photosenses in a respective subrange, and the subranges of at least two of the cells are different from each other.

As described in greater detail below, sensing components 56, 58, and 60 can each be implemented with any suitable excitation or illumination technique to cause emanation of light from objects. One such technique, for example, is enhanced light-target interaction, which can be accomplished by anti-resonant waveguide techniques or other suitable excitation techniques. An "excitation component" is a component that provides excitation to objects so that photons are emitted from the objects; the excitation could, for example, be electromagnetic wave excitation or a reagent. An "illumination component" is a component that provides light, such as to cause emission or scattering of photons from illuminated objects. An illumination component can include one or more sources of light, each of which provides light.

Enhanced light-target interaction is especially important if analyzer 10 is characterizing single particles or low concentrations of biological or chemical agents. In general, an anti-resonant waveguide has a core region surrounded by a cladding layer with a higher refractive index than the core region. Where the core region is a fluid that contains an analyte, light can be guided within the fluid, permitting photonic interaction over an extended length of a channel such as channel 14. As illustrated in FIG. 1, ICs 66, 68, and 70 are therefore supported on spacers 72, providing a suitable gap between each IC and the respective portion of channel 14 to avoid interference with anti-resonant waveguiding.

Anti-resonant waveguide techniques are described in greater detail in co-pending U.S. patent application Ser. No. 10/976,434, entitled "Anti-resonant Waveguide Sensors" and incorporated herein by reference in its entirety. Additional techniques are described in Goddard, N. J., Singh, K., Bounaira, F., Holmes, R. J., Baldock, S. J., Pickering, L. W., Fielden, P. R., and Snook, R. D., "Anti-Resonant Reflecting Optical Waveguides (ARROWs) as Optimal Optical Detectors for MicroTAS Applications", dias.umist.ac.uk/NJG/Abstracts/MicroTAS/MicroTas2.htm, pp. 1-5, and Singh, K., and Goddard, N. J., "Leaky Arrow Waveguides for Optical Chemical and Biosensors", (Abstract Submitted to Biosensors 1998), dias.umist.ac.uk/NJG/Abstracts/Biosensors/ARROW-Biosensors.htm, pp. 1-2, both of which are incorporated herein by reference.

In optical biosensors, the interaction between light and target molecules is typically very weak. Techniques in which light propagates in a longitudinal direction, such as anti-resonant waveguide techniques, can improve the interaction because of the extended length in which interaction occurs. Also, such techniques are very suitable for multi-signal analysis because they are relatively unaffected by changes in wavelength or film thickness. More particularly, in contrast to excitation techniques that use evanescent fields of ordinary waveguides and therefore require very small channels, fluidity channels with maximum transverse dimensions as great as a few millimeters can be used as anti-resonant waveguides. Suitable configurations can include, for example, an aerosol in a glass capillary tube or a liquid film between glass slides. The excitation could be with visible light, ultraviolet light, infrared light, radiation in the terahertz range, or any other appropriate electromagnetic radiation. Examples of specific sensing components employing anti-resonant waveguide techniques are described in greater detail below.

The use of anti-resonant waveguides and other techniques for enhanced light-target interaction may require additional mechanisms to suppress background excitation light. The use of an anti-resonant waveguide, by itself, strongly reduces background detected by a photosensor array located parallel to the waveguide, as illustrated below. In addition, if each cell of a photosensor array is only photosensing a subrange of photon energies, additional background suppression occurs because other photon energies will not be photosensed; in some implementations, for example, they may be reflected from a coating over the photosensor array. Additional background suppression can be obtained using a wavelength filtering component as part of the wall of channel 14 or as an additional coating on top of a photosensor array.

FIG. 2 shows schematically a cross section of analyzer 10 taken along the line 2-2 in FIG. 1. Although FIG. 2 therefore shows features of second fluorescence component 58, similar features would be found in first fluorescence sensing component 56 and, to an extent, in Raman scatter sensing component 60.

As object 16 travels through portion 80 of channel 14 in the downstream direction indicated by arrow 82, it receives light from an excitation component, illustratively light source 84 which could be a laser or an LED, for example; in general, excitation radiation in any of various different energy ranges can be coupled into channel 14 to produce anti-resonant waveguiding. Portion 80 can function as an anti-resonant waveguide in response to light from source 84, or it can function in another way that provides enhanced light-target interaction. For example, other techniques that provide continuous excitation to a fluorescing molecule include tracking the molecule in motion with a scanning laser beam; using a linear array of LEDs to sustain particle excitation along its path; arranging a collimated beam along the particle path without waveguiding; and providing a Fabry-Perot-style cavity in which light passes through the medium containing the particle several times.

Sensing components using anti-resonant waveguide modes are especially advantageous in combination with fluidity devices because the fluidity channels themselves can be used as anti-resonant waveguides in various configurations. Examples of configurations include an aerosol carrying analytes in a capillary, a liquid film carrying analytes within a channel or between glass slides, etc.

In response to light from source 84, an analyte within object 16 fluoresces, emitting light with a characteristic spectrum of photon energies. A portion 86 of the light is emitted toward assembly 87, which includes at least IC 68 and possibly also other structures. Photons in portion 86 can therefore be photosensed by cells of a photosensor array on IC 68. Assembly 87 is positioned so that the photosensor array on IC 68 is close to and parallel to the path of object 16 through portion 80, to increase light collection efficiency.

A photosensor array is "positioned along" or "along" a channel or a portion of a channel if the array is positioned near the channel or portion in such a way that one or more of its photosensors can photosense light emanating from the channel or portion.

Assembly 87 is illustratively supported on spacers 72 to avoid disturbing anti-resonant waveguiding in portion 80 of channel 14. Spacers 72 are positioned outside portion 80, and, as a result, air gap 88 below assembly 87 prevents disturbance of waveguiding because air has a lower refractive index than that of the liquid within the waveguide. Any other appropriate structure could be provided that would prevent disturbance of waveguiding; examples include a gas or vacuum layer or possibly even a liquid layer or film with a low refractive index. A thin gap, layer, or film that is only a few microns thick, e.g. 10 μm, is sufficient to prevent disturbance of waveguiding if it has a sufficiently low refractive index.

Because object 16 receives excitation continuously throughout portion 80, fluorescence also occurs continuously along the photosensor array. As a result, spectral information is collected continuously as object 16 moves through portion 80. As described below, a similar technique can be used for light scattered by object 16.

The structure shown in FIG. 2 could also be used to implement Raman scatter sensing component 60 in a way that, although not comparable to dedicated Raman sensors, may provide acceptable performance and resolution with sufficient spectral range for a given application such as for specific Raman bands of interest. The output signal could indicate a set of intensity ratios of selected Raman lines and/or certain narrow intervals of a Raman spectrum rather than a complete Raman spectrum. By focusing on key differentiators in a Raman spectrum, this technique could provide the most relevant input for data analysis and comparison against a library of Raman profiles or another such database. This approach may be more tractable and efficient as a first step than comparing an entire Raman spectrum with a huge library of profiles.

To implement a Raman scatter sensing component as shown in FIG. 2, it would be necessary that light source 84 and IC 68 meet appropriate specifications, especially with regard to sensitivity and background light suppression within analyzer 10. In addition, suitable optical elements would be necessary between channel 14 and the photosensor array of IC 68 to ensure efficient and suitable light sampling.

Exemplary differences between a fluorescence sensing component and a Raman scatter sensing component would be as follows: A fluorescence sensing component could include a photosensor array in which cells photosense within a wide spectral range with rather low resolution, e.g. 400-700 nm with a moderate wavelength resolution of 2-5 nm. In contrast, a Raman scatter sensing component could include a photosensor array in which cells photosense within a smaller spectral range close to the excitation wavelength but with greater resolution, e.g. 800-830 nm with a resolution of 0.2-0.5 nm or even higher resolution. The sensing range for Raman scatter sensing must be set in accordance with typical energies of Raman scattered photons, which are 100 $cm^{-1}$ to a few 1000 $cm^{-1}$ wavenumbers different from the excitation photon energy, where wavenumber k=2π/λ in units of 1/cm.

FIG. 2 also illustrates one of the ways in which support structure 12 could be implemented. Support layer 90 could, for example, be a light-transmissive glass or silicon substrate. Channel 14 can be defined in a micromolded layer 92 of polydimethylsiloxane (PDMS). PDMS is an inexpensive, biocompatible, transparent, silicon based elastomer with controllable hardness, hydrophobicity, excellent gas permeability, and surface chemistries that can be tuned to specific applications. It is sufficiently transparent in the visible portion of the spectrum to allow visualization of fluidity transport and measurements through a portion of layer 92, such as by a photosensor array on IC 68. In patterning layer 92 and other layers in FIG. 2, the length of channel 14 in which light-target interaction occurs can be chosen to minimize interference between different analytes.

Techniques for producing a patterned layer of PDMS are described, for example, in Becker, H., and Gartner, C., *Electrophoresis*, Vol. 21, 2000, p. 12, incorporated herein by reference. For example, a template can be fabricated on glass from SU-8 polymer, and PDMS can then be deposited to form a patterned structure within the template. The template can then be removed. Over layer 92 is a plate 94, such as glass and therefore another example of a light-transmissive structure.

A structure that "transmits" photons, sometimes referred to herein as "light-transmissive", is any material structure through which light can propagate. It is not necessary that there be a one-to-one relationship between photons that enter a light-transmissive structure and photons that exit from it as long as the structure provides exiting photons in response to entering photons as a result of light propagation through the structure.

More generally, to "transmit" photons is to perform a function by which exiting photons at an exit position are provided in response to entering photons at an entry position as a result of light propagation between the entry and exit positions.

The use of a patterned layer of PDMS is merely illustrative. A wide variety of other techniques could be used to produce microchannels or other channels suitable for analyzer 10. For example, techniques could be used that etch glass to produce channels. Also, channels could be microfabricated by patterning a layer of a polymer material such as SU-8 to produce high aspect ratio channel walls. Depending on the medium that carries analyte through channel 14, parameters of channel 14 can be modified for optimal results. If the medium is an ordinary fluid, for example, the optimal width of the channel will be different than if the medium is an aerosol. It may also be necessary to adjust the width of the channel to obtain a desired throughput.

Other dimensions of the structure shown in FIG. 2 can be changed to obtain desired results. For instance, the thicknesses of layers 90 and 94 can bear a desired relationship to the height of channel 14, depending on various constraints, including stability requirements, manufacturing convenience, and, as noted below, the need to accommodate a desired flow of fluid and objects through channel 14. Thicknesses of layers 90 and 94 are often greater than or approximately equal to the height of channel 14. Typical thicknesses range between approximately 100 μm and 2 mm. Channel height ranges from approximately 1 μm or less up to a few mm.

A specific parameter of channel 14 that can have significant effects is adhesiveness of the channel wall. For example, experiments with *B. Thurengiensis* on uncoated surfaces have shown that adhesion may be a concern. This would be especially important for microfluidic channels, i.e. channels with maximum transverse inner dimensions less than 0.1 mm—their characteristically high surface area to volume ratio could lead to significant system loss. Bioadhesion could also compromise the ability to track the passage of a sample analyte through the entire length of channel 14. Bioparticles are attracted to charged or highly polarized surfaces such as glass, plexiglass acrylic, silicon, and even polymeric materials. With prolonged contact, bacteria and proteins may adhere to almost any surface by exposing more of their hydrophobic core regions, thus adapting their contact area to the specific surface properties. Once such a molecule is sufficiently close (e.g. 1-10 nm) to any surface, van der Waal's force dominates, and adhesion becomes a significant issue.

Various techniques can be used to reduce sample loss through surface adhesion, such as by providing barriers that prevent bioparticles from coming too close to the surfaces. More specifically, an anti-adhesive coating can be applied to prevent bioparticles and other analytes from sticking to the walls. Dip-coated polyethylene glycol (PEG) is a good choice for preventing adhesion of most biomaterials such as bacteria and proteins. In addition, PEG may be very well suited for microfluidic devices, since PEG can maintain capillary force on aqueous solutions. Other coatings may be viable options depending on sample properties, material interface chemistry, and operating conditions and regimes; for example, parylene C or vapor deposited tetraglyme might provide appropriate coatings. As noted above, anti-resonant waveguiding techniques can employ a channel with an inner diameter at least up to approximately 1.0 mm and possibly greater, in which case adhesion is not as great a problem and clogging is unlikely to occur; nevertheless, anti-adhesion measures may be advantageous to prevent spurious background signals emitted by material adhering to a channel's inner wall.

FIG. 2 also shows optical component 96 on the side of support layer 90 opposite PDMS layer 92. Optical component 96 provides an appropriate surface 98 through which light from source 84 can be coupled into the anti-resonant waveguide within portion 80 of channel 14. Although shown as separate layers in FIG. 2, support layer 90 and optical component 96 could instead be fabricated from a single layer of material by suitable processes.

FIG. 3 is a schematic view of an implementation of assembly 87 in which IC 68 includes photosensor array 100 and also has spacers 72 attached to it, such as after microfabrication of array 100 and other components. Photosensor array 100 is illustratively a two-dimensional array, with at least two rows of cells that include photosensors.

Different rows or other parts of photosensor array 100 can be provided with different coatings or can be otherwise structured so that their cells photosense different ranges or subranges of photon energies. As a result, the information obtained from a single IC can provide a detailed analysis of incident photons over a broad range of photon energies. In addition, reference cells, such as the cells in row 102, can be used to provide a spatially resolved real-time reference signal, such as to continuously monitor position of an object emanating light as it moves past array 100.

Each cell in row 102 photosenses photons throughout a suitable range, characterized as $\lambda_{all}$, to produce a reference for a nearby cell in row 104. For implementations in which it is advantageous to have signal strengths of the same order from a cell in row 102 and its paired cell in row 104, the cell in row 102 must be different from the cells in row 104. For example, it could have a different sensing area or it could have a gray filter coating different than a coating over the paired cell in row 104.

Each cell in row 104, on the other hand, photosenses a respective subrange between $\lambda_{min}$ and $\lambda_{max}$, with illustrative cell 106 photosensing a subrange centered around $\lambda_p$. IC 68 also includes array circuitry (not shown) as well as peripheral circuitry 110 which perform various functions relating to readout of photosensed information from array 100.

One advantage of the technique illustrated in FIG. 3 is that IC 68 provides a compact photosensor array that can be used for various functions within a system such as analyzer 10. The compactness of IC 68 also allows for an interactive detection scheme. Subsequent or adjacent ICs within analyzer 10 may exchange information or trigger events. The combination of analysis results from several ICs within analyzer 10 may help to obtain orthogonal information and ultimately enable reliable identification of object 16.

Various criteria could be used to characterize techniques with longitudinal light propagation. One useful criterion is the proportion of light intensity that occurs in fluid. In other words, in any given cross section of a channel or channel portion, a total light intensity of longitudinally propagating light can be integrated over the entire cross section, including the material around the boundary, and a partial light intensity can be integrated solely over the area within the boundary, i.e. the area that can contain fluid. The ratio of the partial light intensity to the total light intensity is a proportion that can be expressed, for example, as a percentage. In general, a proportion N of light intensity "occurs" in fluid if the ratio of partial to total light intensity obtained in this manner is N.

FIG. 4 shows a cross section of channel 14 along the line 4-4 in FIG. 2. As in FIG. 2, assembly 87 is separated from layer 94 by gap 88, due to spacers 72.

Layers 90 and 94 provide the upper and lower boundaries of channel 14, and the lateral boundaries are provided by walls 120 and 122 formed in layer 92 (FIG. 2). As indicated by the axis in FIG. 4, width W of channel 14 can be treated as extending in the x-direction, while height H can be treated as extended in the z-direction, with the lower surface of layer 90 arbitrarily being at z=0, the upper surface being at $z=Z_1$, and the lower surface of layer 94 being at $z=Z_2$. The specific relation of W to H in FIG. 4 is merely illustrative; for example, various W/H ratios can be used in anti-resonant waveguides, such as 2, 4, or 10. As noted above, however, the height H must be sufficiently large to accommodate the desired flow or throughput of fluid and objects through channel 14 and to avoid blockage, such as due to adhesion. Also, the ratios $Z_1/H$ and $Z_2/H$ can be adjusted to obtain stability and manufacturing convenience.

FIG. 5 illustrates exemplary distributions of light intensity that might occur across channel 14 along the z-direction. Curve 126 shows a Gaussian distribution resulting from excitation of a first anti-resonant waveguide mode, possible for a small channel and with a precisely coupled illumination; a number of other specific modes are described in co-pending U.S. patent application Ser. No. 10/976,434, entitled "Anti-resonant Waveguide Sensors" (the "Anti-resonant Waveguide Application"), and incorporated herein by reference. Curve 128, on the other hand, shows a nearly uniform distribution within the channel resulting from excitation of many modes, as could occur in a larger channel with uncollimated illumination.

For curve 126, very little light intensity occurs in each of layers 90 and 94, while 90% or more of the light intensity occurs in fluid in channel 14, where $Z_1<z<Z_2$. At approximately the center of the channel, where $z=(Z_1+Z_2)/2$, the light intensity is at its maximum $I_{max}$. The light is effectively confined or guided within the lower refractive index core between regions with higher refractive indices. Since the light is guided in the area in which objects of interest may interact with the light, most of the available light intensity can be used for excitation by illumination.

For curve 128, on the other hand, a significant amount of light intensity occurs in each of layers 90 and 94, but still a significant part of the light intensity, such as 40% or 50%, occurs in fluid in channel 14, where $Z_1<z<Z_2$. There is no identifiable maximum intensity, and the light is not as effectively confined or guided within the core as with curve 126, but it is more homogeneously distributed across the width of channel 14, which may be advantageous for some applications. Despite less effective confinement, a significant part of the available light intensity can be used for excitation by Illumination.

The indices of refraction of layers 90 and 94 and of walls 120 and 122 are all at least slightly greater, and possibly considerably greater, than that of the fluid contained in channel 14, an arrangement that permits generation of an anti-resonant wave within channel 14 if illuminated at an appropriate angle of incidence, as discussed in greater detail below. For example, the indices of refraction of layers 90 and 94 and of walls 120 and 122 might be between 1.4 and 1.8, while the index of refraction of the fluid might be between 1.2 and 1.4; other indices across a wide range are also possible. For even higher indices of refraction in special cases or applications, semiconductor materials might be used, such as silicon, gallium arsenide, gallium nitride, or zinc oxide; silicon, for example, might be suitable for very small channels and infrared illumination.

In general, the greater the difference between the refractive indices of boundary material (in layers 90 and 94 and in walls 120 and 122) and fluid in channel 14, the greater is the confinement factor of anti-resonant waveguiding. But waveguiding requires that the refractive index of the fluid must be larger than that of the medium outside the boundary material, and the medium is ordinarily air with refractive index $n_A=1$.

Figure 4:
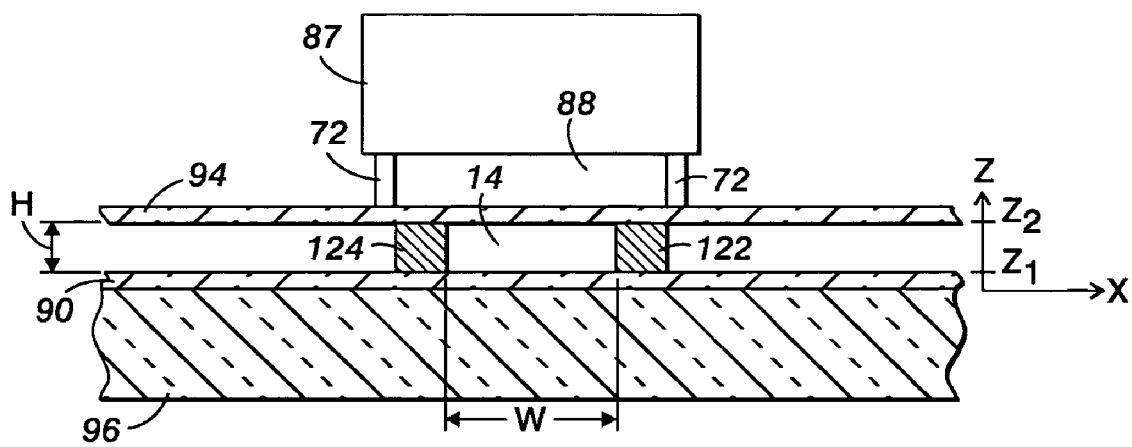
FIG. 4 is a schematic cross-sectional view of the analyzer in FIG. 1, taken along the line 4-4 in FIG. 2.
Figure 5:
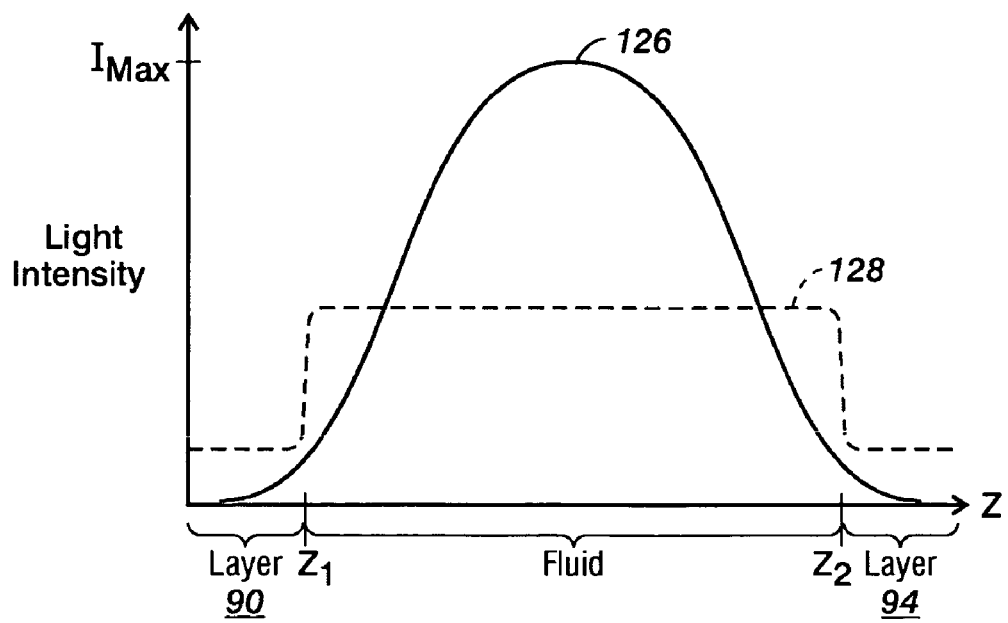
FIG. 5 is a graph illustrating light intensity as a function of position in the z-direction in FIG. 4.

Performing the calculations set forth in the Anti-resonant Waveguide Application, the Eigensolutions or optical modes for the waveguide structure illustrated in FIG. 4 can be obtained, enabling computation of indices of refraction and modal confinement factors of the modes. Each such mode can be excited or coupled by light entering the waveguide at a specific angle of incidence corresponding to the effective refractive index.

The confinement factor of a mode corresponds to the fraction of the light intensity confined within the boundary of the waveguide, i.e. within channel 14. As explained in the Anti-resonant Waveguide Application, a mode can be selected with a desired confinement factor, up to and possibly greater than 90%. To be useful, such a mode must have an effective refractive index close to, and typically slightly smaller than, the refractive index of the core material, illustratively the fluid in channel 14. When the core thickness H is large compared with the wavelength of propagating light, the effective refractive indices of these modes approach the refractive index of the core.

Figure 6:
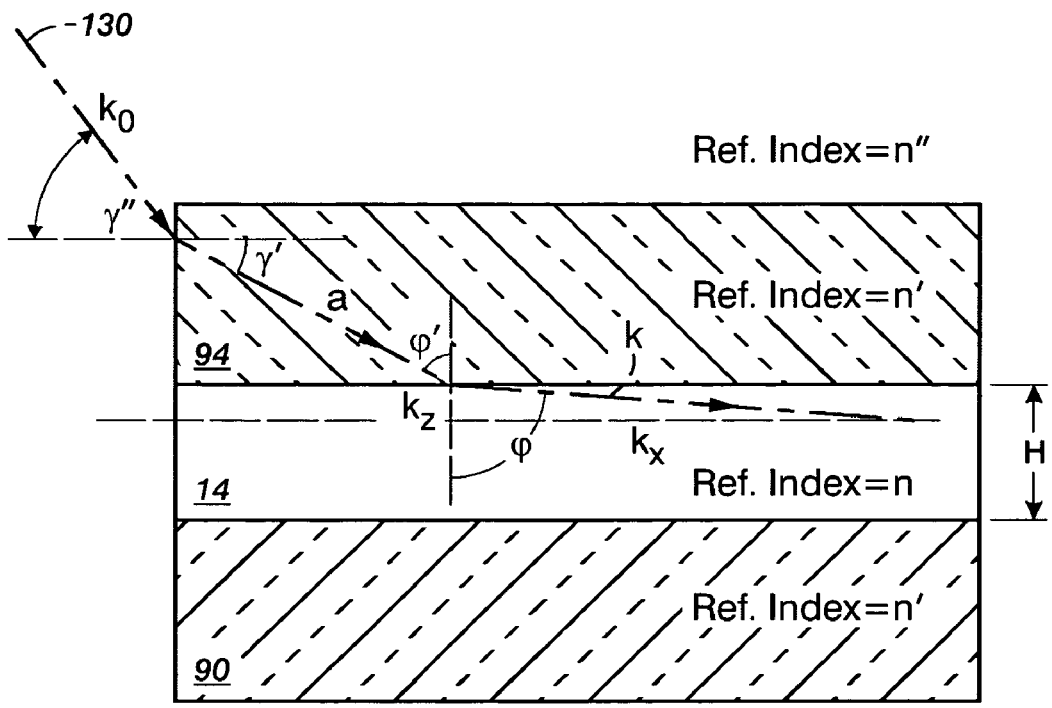
FIG. 6 is a schematic cross-sectional view similar to that in FIG. 2, illustrating entry of light through an end facet.

FIG. 6 illustrates schematically how light provided to an end facet of channel 14 could result in longitudinal propagation of light in an anti-resonant waveguide mode. As shown, the refractive index of the fluid in channel 14 is n, the refractive indices of layers 90 and 94 are both n', and the refractive index of the surrounding air is n"=1. An optimum angle of incidence γ" of representative incident light ray 130 can be derived in the manner set forth in the Anti-resonant Waveguide Application.

Figure 7:
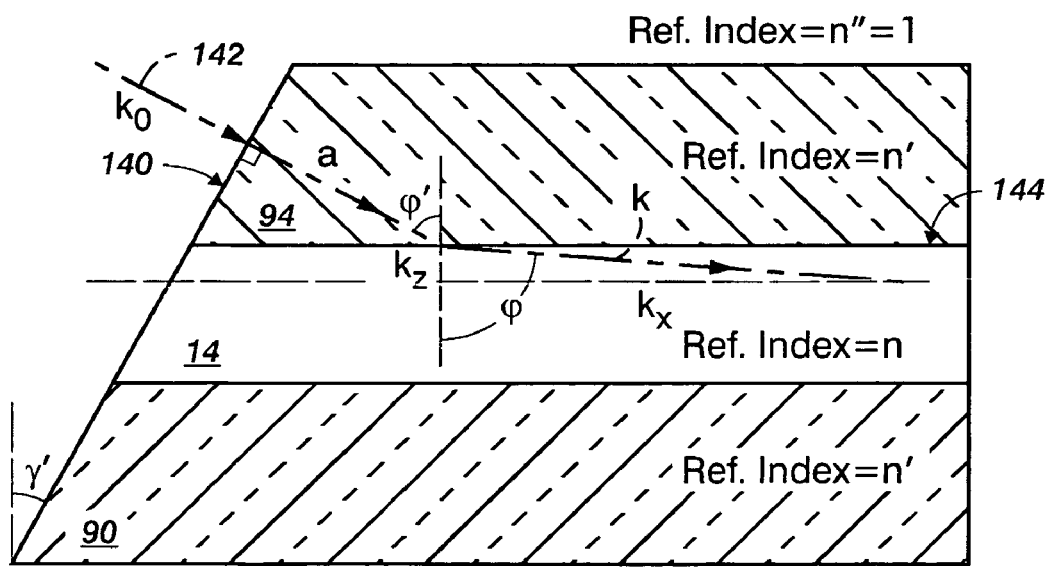
FIG. 7 is a schematic cross-sectional view similar to FIGS. 6, illustrating entry of light through an obliquely angled end facet.

FIG. 7 schematically illustrates an alternative implementation with an oblique exterior surface 140 similar to that shown in FIG. 2, at an angle of γ'=90°−φ' from the position of the facet in FIG. 6. The implementation in FIG. 7 minimizes losses caused by large angles of incidence like that of ray 130 in FIG. 6. Reflections at surface 140 are minimized if incident light ray 142 enters at or near a normal to surface 140. By adjusting the angle of surface 140 relative to the z-direction shown in FIG. 4, ray 142 can enter surface 140 and still strike the interface 144 between layer 94 and the fluid in channel 14 at an angle suitable to couple to an anti-resonant waveguide mode.

Figure 8:
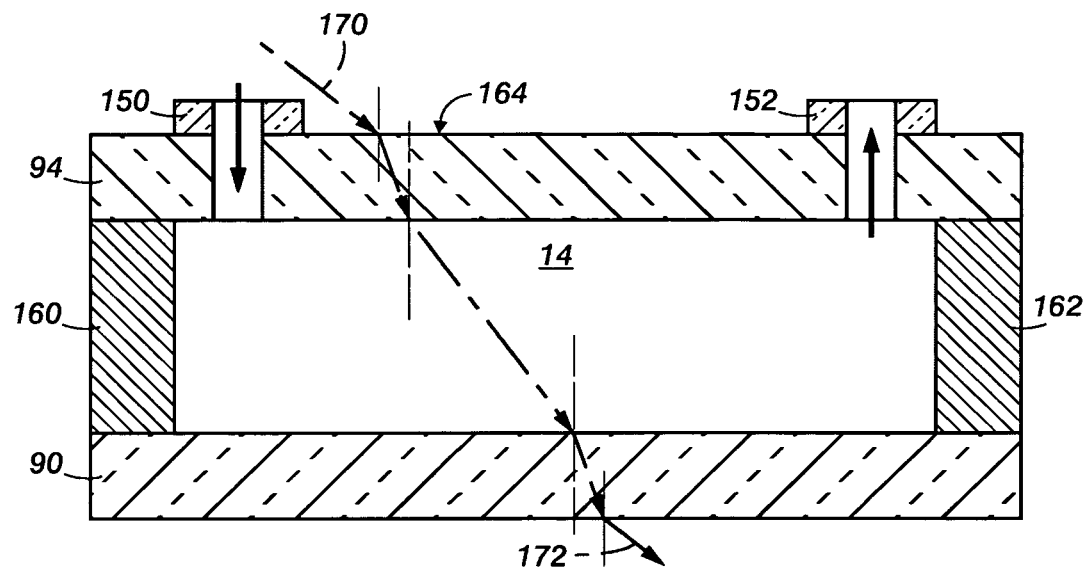
FIG. 8 is a schematic cross-sectional view of an alternative implementation in which a channel as in FIG. 2 is illuminated through a light-transmissive structure along its boundary.

FIG. 8 illustrates a problem that arises where it is impractical to illuminate channel 14 through a facet surface as in FIGS. 6 and 7. The only portion of channel 14 capable of functioning as an anti-resonant waveguide is the portion between inlet port 150 and outlet port 152. In addition, the implementation of FIG. 8 includes end components 160 and 162, which can include the same material as layer 92 or other suitable material such as Gelpak® film, PDMS, SU-8 or other photoresist material, glass, or quartz. End components 160 and 162 interfere with illumination through end facet surfaces, which would also be true if they were instead connected as entry and exit ports.

Since layer 94 (and, more generally, all the material bounding portions of channel 14 that can function as anti-resonant waveguides) is light-transmissive, it is possible to illuminate channel 14 by providing light to the upper surface 164 of layer 94. As illustrated, however, for light ray 170, the angle of incidence is inappropriate for coupling to an anti-resonant waveguide mode of channel 14. Instead, most of the light provided through ray 170 is transmitted through layer 94, through the fluid in channel 14, and through layer 90, exiting as ray 172.

Figure 9:
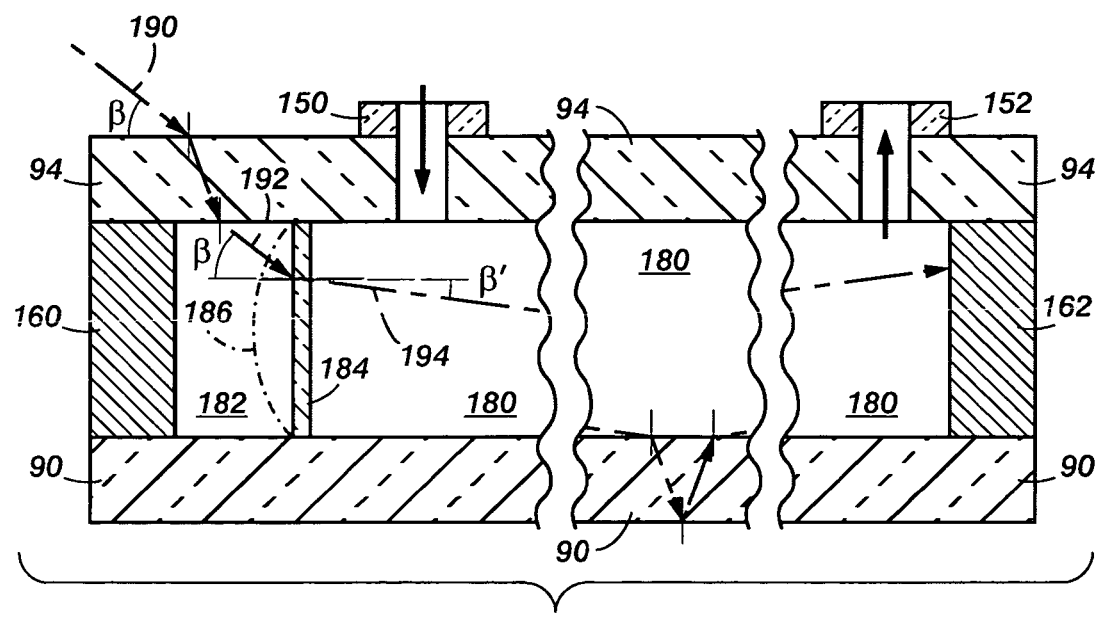
FIG. 9 is a schematic cross-sectional view of a further alternative implementation in which illumination through a light-transmissive structure as in FIG. 8 can couple to an anti-resonant waveguide mode.

FIG. 9 illustrates an alternative implementation in which channel 14 includes two portions, with portion 180 capable of containing fluid and with portion 182 containing air. Portions 180 and 182 are separated by bounding component 184, which can include the same or similar materials to those of end components 160 and 162, but, as shown, can be as thin as possible for optical purposes while being sufficiently thick to be manufacturable and to preserve a fluidity barrier between portions 180 and 182. As a result, portion 182 is a projection of portion 180 beyond bounding component 184, which also functions as an end component for portion 180. Bounding component 184, as suggested by dashed line 186, can alternatively have a convex surface disposed toward portion 182, so that light entering from portion 182 is focused or, in the case of divergent light such as from a poorly collimated LED source, becomes more collimated.

As illustrated by incident light ray 190, light entering the upper surface 164 of layer 94 at an appropriate angle of incidence β then enters portion 182 after traveling through layer 94. The angle of ray 192 in portion 182 is also β if portion 182 contains air and will be approximately the same if portion 182 contains a gas or a vacuum; in other cases, the angle of ray 192 may be modified due to difference in the index of refraction between portion 182 and exterior air. Ray 192 then enters bounding component 184, which is also light-transmissive, so that ray 194 exits into portion 180 at an appropriate angle of incidence β' to couple to at least one anti-resonant waveguide mode; with the illustrated geometry, $\beta'=\arcsin((n_A/n_L)\sin \beta)$, where $n_A$ and $n_L$ are the refractive indices of air, gas or, vacuum in portion 182 and fluid in portion 180, respectively.

Figure 10:
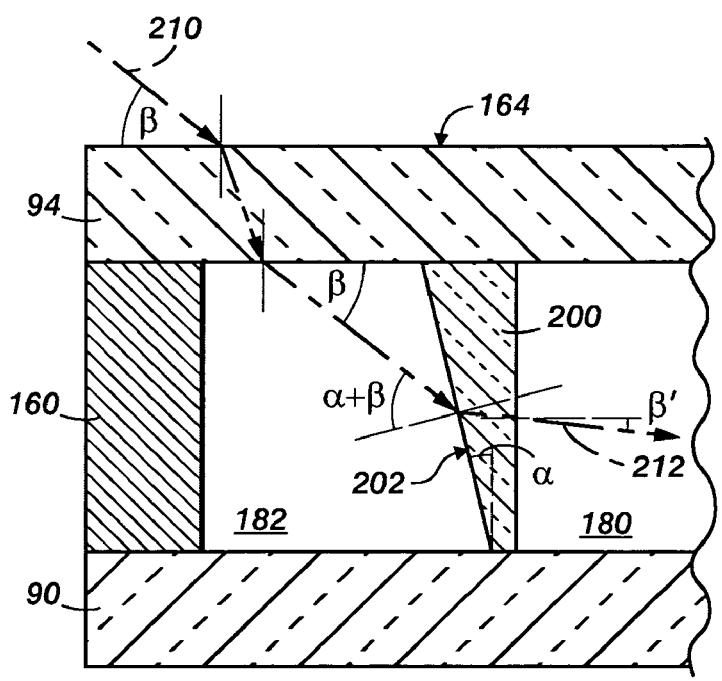
FIG. 10 is a schematic cross-sectional view illustrating a further alternative implementation to that of FIG. 9.
Figure 11:
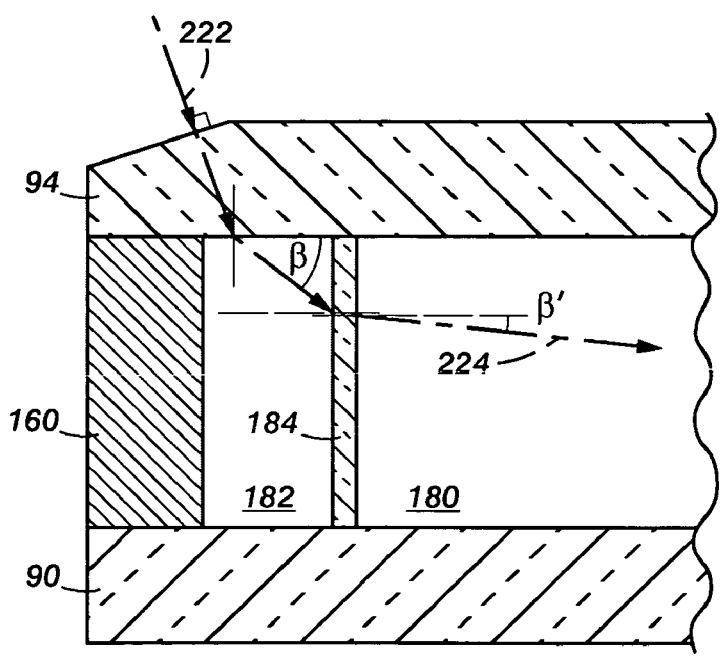
FIG. 11 is a schematic cross-sectional view illustrating a further alternative implementation to that of FIG. 9.

As shown In FIG. 9, ray 194 is nearly parallel to the longitudinal direction, which can be desirable to couple with some anti-resonant waveguide modes. Also, rather than exiting from layer 90, ray 194 is reflected, so that light propagates longitudinally within portion 180. FIGS. 10 and 11 illustrate other, similar techniques in which a ray nearly parallel to the longitudinal direction can be obtained while reducing reflection losses. For example, an angle of approximately 2° or less can be obtained.

FIG. 10 shows an alternative implementation to that in FIG. 9. In FIG. 10, channel portions 180 and 182 are, as above, rectangular in cross section and are separated by bounding component 200, which is differently shaped than bounding component 184 in FIG. 9. Specifically, surface 202 of component 200, the surface disposed toward portion 182, extends in an oblique direction at an angle a from a transverse direction, so that surface 202 functions as an oblique light entry surface even though it is not an exterior surface, increasing coupling angle and decreasing reflection losses. With this geometry, $\beta'=\arcsin\{(n_B/n_L)\sin[\arcsin((n_A/n_B)\sin(\alpha+\beta))-\alpha]\}$, where β is the incident coupling angle of ray 210 and β' is the angle of ray 212 from the longitudinal direction in channel portion 180 and where $n_B$ is the refractive index of the material of bounding component 200. Due to the oblique angle of surface 202, coupling angle β can be increased without loss of efficiency, and increasing β in turn decreases reflection losses at surface 164.

FIG. 11 shows another alternative implementation to that in FIG. 9, an alternative that could also be combined with the technique in FIG. 10 to further reduce reflection losses. In FIG. 11, layer 94 has an oblique exterior light entry surface in the form of wedge facet 220, and ray 222 enters layer 94 at or near a normal to facet 220 reducing reflection and allowing a steeper angle of incidence than the angle β in FIGS. 9 and 10 while still providing ray 224 nearly parallel to the longitudinal direction in portion 180. Techniques similar to that of FIG. 11 could also be used to combine an oblique exterior light entry surface as in FIG. 2 or FIG. 7 with a bounding component as described in relation to FIGS. 9 and 10.

In some applications, it may be desirable to excite only one or a small number of anti-resonant waveguide modes, while in others it may be desirable to excite many modes. In general, incident light couples with fewer modes if it is highly collimated so that it has a narrow range of angles of incidence. On the other hand, less collimated incident light is more effective to excite a larger number of modes, such as for more homogeneous light intensity distribution across a channel. The technique of FIG. 10 is especially suitable for collimated light sources such as lasers. More generally, techniques that provide light nearly parallel to the longitudinal direction tend to couple with modes that have higher confinement factors, so that the techniques in FIGS. 9-11 can be used to increase the proportion of light propagating within the fluid.

A technique similar to those illustrated in FIGS. 9-11 has been demonstrated by coupling ultraviolet light to anti-resonant waveguide modes through an airhole. In the demonstration, fluorescin inside a fluidity chamber was efficiently excited and emitted green fluorescent light.

FIGS. 9-11 illustrate only a few implementations of a type of technique, and various other modifications could be made. For example, portion 182 could contain vacuum, a gas other than air, or other solid or fluid material with a lower refractive index than the surrounding material of layers 90 and 94. Similarly, a wide variety of materials could be used to provide bounding components and end components; like other materials bounding portions of channel 14 that function as anti-resonant waveguides, these materials should be light-transmissive with little or no absorption or fluorescence for the incident light, and could ideally, for optimum efficiency, be transparent.

While applicable to excitation of fluorescence, the techniques of FIGS. 9-11 can also be used in other illumination applications. More generally, FIGS. 12 and 13 illustrate applications other than fluorescence in which techniques as described in relation to FIGS. 4-11 could be used.

Figure 12:
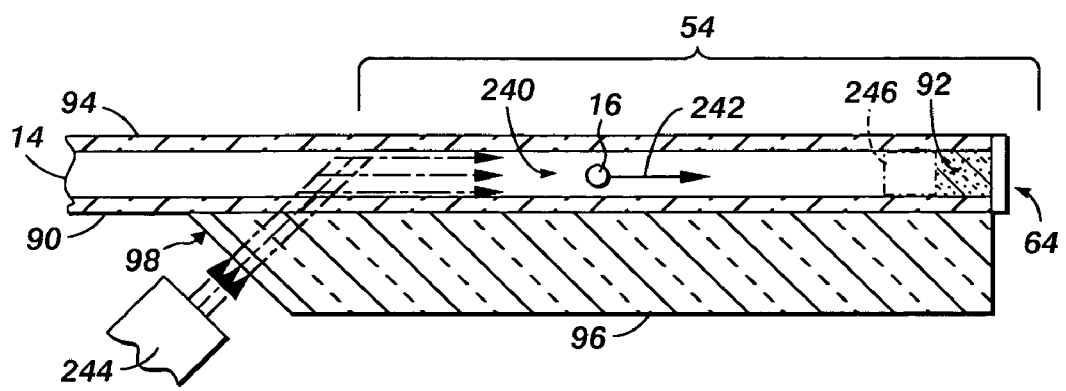
FIG. 12 is a schematic cross-sectional view of the analyzer in FIG. 1 taken along the line 12-12.
Figure 13:
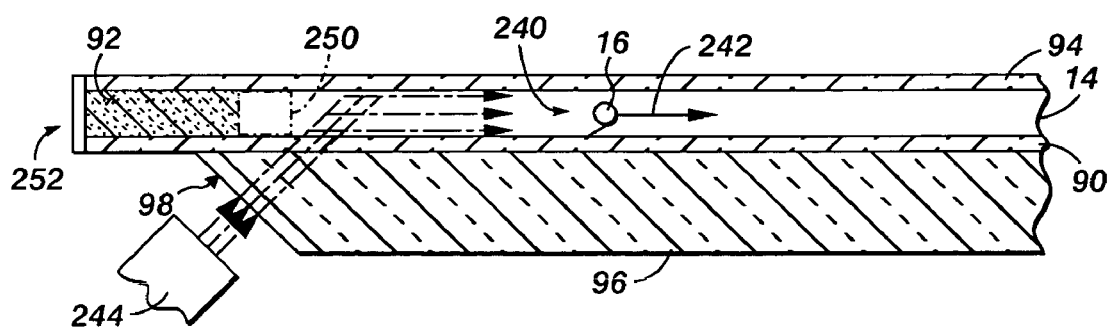
FIG. 13 is a schematic cross-sectional view similar to that of FIG. 12 for a backscatter sensing component.

FIG. 12 shows schematically a cross section of analyzer 10 taken along the line 12-12 in FIG. 1. FIG. 12 therefore shows several features of optical absorption sensing component 54, including IC 64, which is shown by itself, but would be implemented within an assembly, such as any of the implementations of assembly 87 as described above.

As object 16 travels through portion 240 of channel 14 in the downstream direction indicated by arrow 242, it receives light from an excitation component, illustratively light source 244 which is a suitable broadband illumination component such as a white light source and which could be an LED or a halogen lamp. Light from source 244 could be provided in any suitable way, including the ways described above in relation to FIGS. 4-11. As in FIG. 2, portion 240 can function as an anti-resonant waveguide in response to light from source 244, or it can function in another way that provides enhanced light-target interaction, as described above.

In response to light from source 244, object 16 scatters or absorbs light, resulting in a modified spectral distribution of transmitted light photosensed by cells of a photosensor array on IC 64. For example, object 16 may contain an analyte that absorbs photons within certain energy subranges, producing an absorption spectral distribution. Because object 16 receives excitation continuously throughout portion 240, cells on IC 64 will continue to photosense the absorption spectral distribution as object 16 passes through portion 240 of channel 14. Then, the spectral distribution will return to its unmodified form when object 16 exits from sensing component 54 through curved portion 246 of channel 14.

FIG. 13 shows schematically a cross section of analyzer 10 taken along a line similar to that of FIG. 12 but through a Raman backscatter sensing component. As suggested by the reference numerals that are the same as in FIG. 12, many features of FIG. 13 are implemented the same as in component 54. For example after entering through curved portion 250 of channel 14, object 16 travels through portion 240 in the downstream direction indicated by arrow 242 and receives light from an excitation component, illustratively light source 244 as in FIG. 12. Portion 240 can function to provide enhanced light-target interaction, as described above.

In response to light from source 244, object 16 (or an analyte in it) performs Raman scattering of light in an upstream direction, referred to herein as backscattering. The backscattering results in a modified spectral distribution photosensed by cells of a photosensor array on an IC within assembly 252, illustratively positioned outside the upstream end of portion 240 of channel 14, but alternatively positioned outside the downstream end if source 244 illuminates portion 240 from the downstream end. Assembly 252 could be implemented with any appropriate structure, including the above-described implementations of assembly 87. Because object 16 receives excitation continuously throughout portion 240, cells on the IC in assembly 252 will continue to photosense the backscattered spectral distribution as object 16 passes through portion 240 of channel 14. Then, the spectral distribution will return to its unmodified form as object 16 exits from the sensing component. As shown, the photosensor array of IC 252 covers the whole end facet of channel 14, including the channel walls; this is necessary because back scattered light may not only propagate freely through liquid in channel 14 but may also be guided within the walls surrounding the liquid, such as in layer 90 and plate 94.

IC 64 and the IC in assembly 252 could each be implemented with the techniques described above in relation to FIG. 3. For example, cells in row 102 of photosensor array 100 could provide reference information for use in correcting position-dependent inhomogeneities resulting from characteristics of channel 14.

Figure 14:
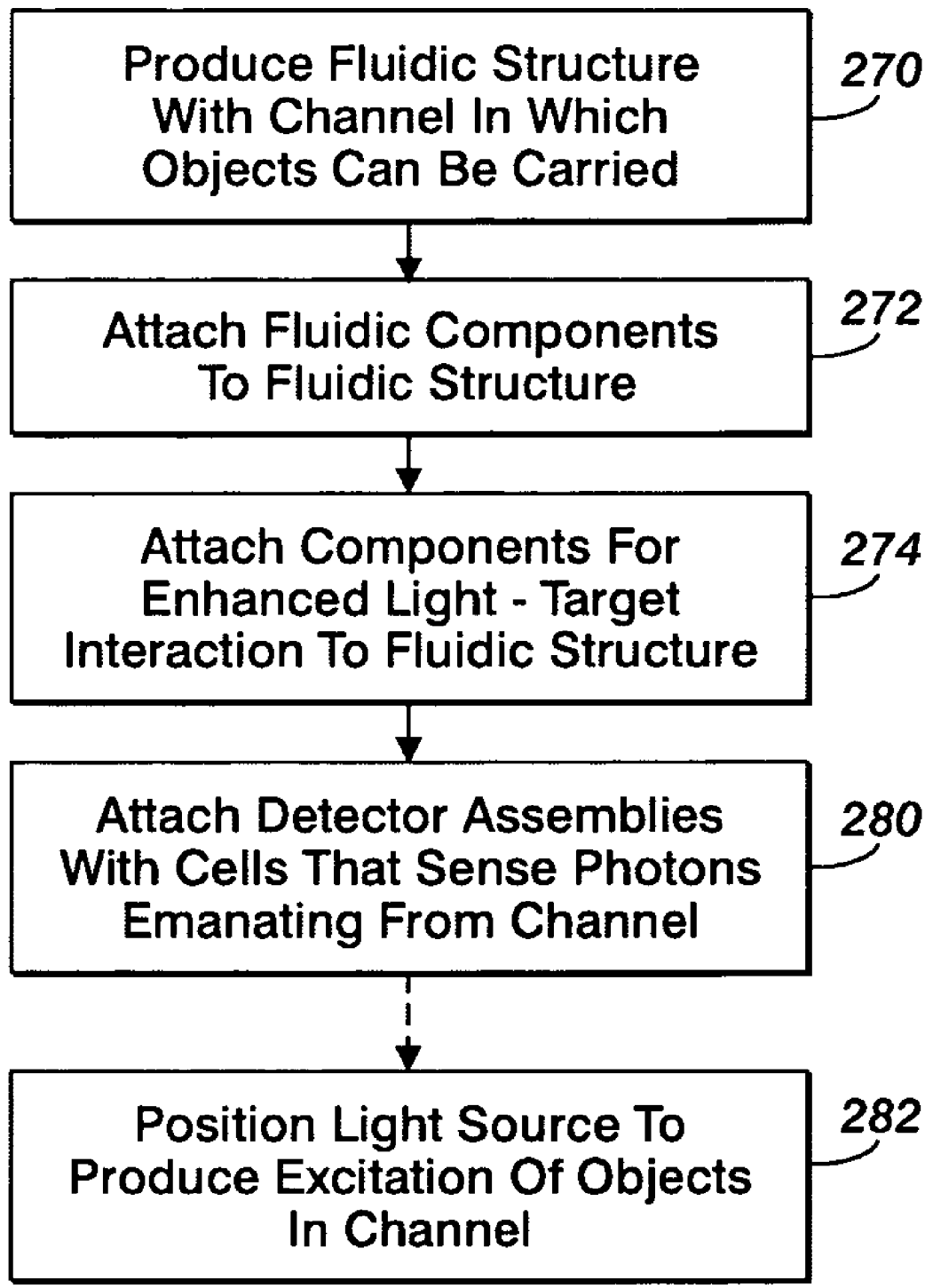
FIG. 14 is a flowchart showing general operations that can be performed in producing an analyzer as in FIG. 1.

FIG. 14 illustrates exemplary operations in producing an analyzer like analyzer 10 in FIG. 1. In particular, the operations in FIG. 14 make it possible to produce apparatus in which a fluidity structure has a channel and a light-transmissive bounding component between first and second portions of the channel, the first of which can contain fluid that enters and exits through ports. The bounding component can be positioned so that light enters the second portion at a first oblique angle, passes through the bounding component, and enters the first portion at a second oblique angle.

The operation in box 270 in FIG. 14 produces a fluidity structure with a channel in a portion of which objects can be carried by fluid. For example, the operation in box 270 could include manufacturing a fluidity structure by positioning or otherwise producing a structured spacer layer between two quartz slides. The spacer layer could be a patterned layer of PDMS, produced as described above in relation to FIG. 2, or could be any other suitable material or combination of materials, including, for example, Gelfilm® or quartz. The operation in box 270 could alternatively be implemented in various other ways, such as by defining a fluidity channel in a quartz slide by glass etching or by molding PDMS to produce a channel, and by then combining the resulting structure with an upper quartz slide. In another alternative, two layers of PDMS could be fabricated on separate substrates and then one could be flipped over and aligned with the other by chip-on-chip assembly. Also, a final substrate of glass, PCB, or PDMS or sufficient hardness could be used to allow direction connection to control and detection measurement circuitry.

The operation in box 270 can include positioning gel or other material within channel 14 as illustrated by bounding component 184 in FIG. 9. This operation involves positioning the material so that light can enter one portion of the channel at a first angle oblique to the longitudinal direction, pass through the bounding component, and enter another portion of the channel at a second angle oblique to the longitudinal direction. In addition, the operation in box 270 can include closing off the ends of a channel with end components such as gel, as illustrated in FIGS. 8 and 9. Also, entry and exit ports can be provided as illustrated in FIGS. 8 and 9.

The operation in box 272 then attaches fluidity components to the fluidity structure produced in box 270. The fluidity components attached in box 272 can include, for example, connectors, tubing, pumps, sensors and so forth. An important function of the fluidity components attached in box 272 is that they can be operated to cause and control movement of objects in the channel. The operation in box 272 can also include attaching wires or other appropriate circuitry to provide signals from a microprocessor or input/output (I/O) device to pumps and other fluidity components.

The operation in box 274 attaches components for enhanced light-target interaction. In the implementation described above in relation to FIGS. 1 and 2, for example, the operation in box 274 can attach optical component 96 on the side of support layer 90, providing an appropriate surface through which light can be coupled into a portion of channel 14 that functions as an anti-resonant waveguide. Similarly, the operation in box 274 can produce spacers 72 to provide a suitable gap that avoids interference with anti-resonant wave guiding; because of spacer, when the IC in detector 87 is later attached with gap 88 between it and the fluidity structure, the IC does not interfere with propagation of light in channel 14. For other techniques to produce enhanced light-target interaction, other suitable components can be attached to the fluidity structure.

The operation in box 280 attaches photosensor arrays with cells that sense photons emanating from channel 14. The operation in box 280 can be implemented by attaching any suitable implementation of detector 87, such as with cells that sense in different subranges and with reference cells, which could be produced as described in more detail in co-pending U.S. patent application Ser. No. 11/316,438, entitled "Photosensing Throughout Energy Range and in Subranges", and incorporated herein by reference in its entirety. The operation in box 280 can also include attachment of wires or any other appropriate form of circuitry such as to provide power and permit a microprocessor or I/O device to read out information from the cells of each photosensor array.

The operation in box 282 can be performed at a different time, as suggested by the dashed line. For example, it could be performed in box 274, or it could be done later, because it is necessary more for operation of the analyzer than for its production. Like the detector, each light source can be attached once, after which it is stationary. In the operation in box 282, one or more light sources are positioned to produce excitation of objects being carried within the channel. For example, the operation in box 282 could include attaching and/or aligning a laser, an LED array, or other light source so that its light is coupled into a portion of the channel functioning as an anti-resonant waveguide. The operation in box 282 can also include attaching wires or other appropriate circuitry to provide signals from a microprocessor or I/O device to light sources.

The technique of FIG. 14 could be modified in many ways within the scope of the invention. For example, the operations in boxes 272, 274, 280, and 282 could be combined in any appropriate way to facilitate attachment of components in a desired sequence. Also, an additional operation could be performed to align or attach interconnects between ICs, gates, and other circuitry, such as connectors to a microprocessor or computer, or this operation could be partially performed in each of boxes 272, 274, 280, and 282. Furthermore, the technique of FIG. 14 is extremely general, and could be employed to produce a wide variety of different fluidity structures with enhanced light-target interaction and detectors. The example illustrated in FIGS. 1 and 2, above, shows how objects carried through a channel can pass through a series of sensing components, each of which includes a respective detector with its own photosensor array, but various other arrangements are possible, examples of which are described below.

FIG. 15 shows an alternative arrangement that could be produced by an implementation of FIG. 14, with components similar to those described above in relation to FIG. 1 having the same reference numerals. As in FIG. 1, first and second fluorescence sensing components 56 and 58 are next to each other in the series of sensing components along channel 14. In addition, however, they are positioned so that IC 290 can be attached over both of them. As a result, the photosensor array of IC 290 includes both cells along channel 14 within component 56 and also cells along channel 14 within component 58. In other respects, the operation of IC 290 can be the same as described above.

FIG. 16 is a cross section along the line 16-16 in FIG. 15, and shows how detector 292 which includes IC 290, can be supported over air gap 88 by spacers 72 in the same manner described above in relation to FIGS. 1 and 2. In general, detector 292 can include any of the features described above in relation to detector 87, but the lateral variation in optical thickness of the transmission structure may be such that the ranges and subranges photosensed within sensing component 56 are different from those photosensed within sensing component 58; alternatively, the ranges and subranges could be the same. An additional important feature is that spacers 72 can help to reduce cross-talk between components 56 and 58 because spacers 72 can be shaped and positioned to act as light-absorbing walls between the two components. In other words, those of spacers 72 that are between components 56 and 58 prevent photons emanating from channel 14 underneath component 56 from propagating to cells of component 58 and vice versa.

Figure 17:
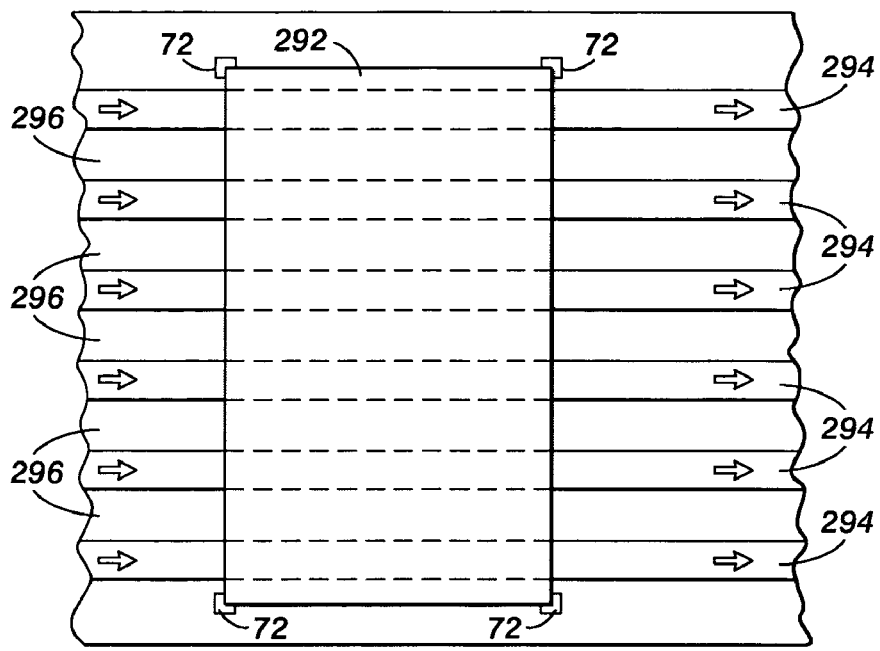
FIG. 17 is a schematic plan view of a portion of an alternative implementation of an analyzer as in FIG. 1.

FIG. 17 shows an alternative arrangement in which detector 292 as in FIG. 14 is positioned over a set of parallel channels 294, which could be produced by producing walls 296 to subdivide a larger channel into subchannels. An advantage of the technique illustrated in FIG. 17 is that several streams of objects can be analyzed in parallel in order to increase throughput or specificity of an analyzer. As mentioned above in relation to FIGS. 15 and 16, laterally varying optical thicknesses of a transmission structure can be produced so that a different range of photon energies is photosensed in each of channels 294, or different subranges are photosensed in different channels, or the same ranges and subranges could be photosensed in all channels.

Figure 18:
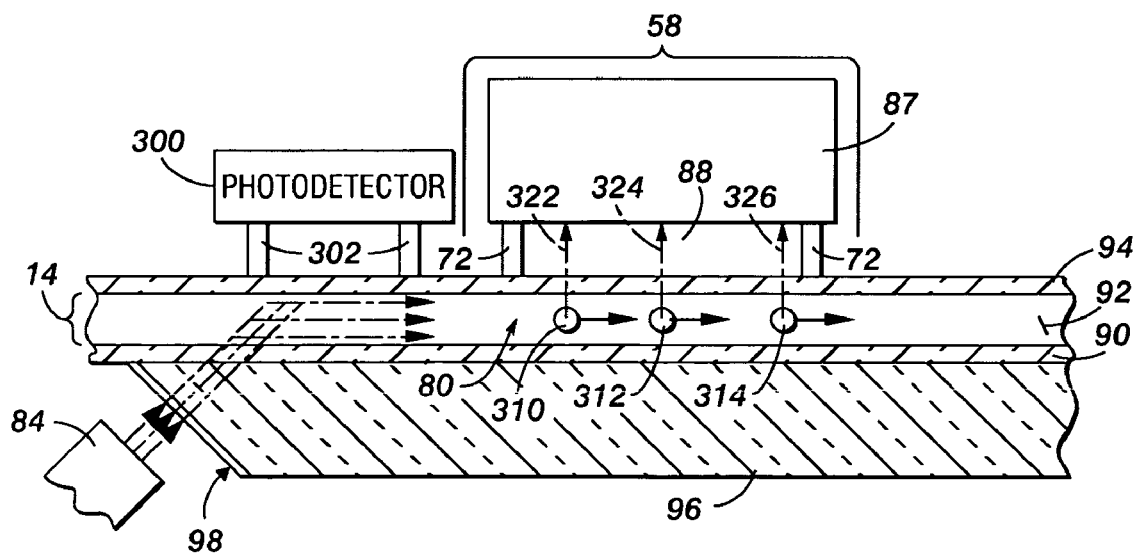
FIG. 18 is a schematic cross-sectional view of an alternative implementation of the sensing component in FIG. 2.

FIG. 18 shows an alternative arrangement that could be produced by an implementation of sensing component 58 in FIG. 2, with components similar to those described above in relation to FIG. 2 having the same reference numerals. As in FIG. 2, portion 80 of channel 14 functions as an antiresonant waveguide in response to light from source 84. Assembly 87 is along portion 80, separated from plate 94 by spacers 72. Upstream from portion 80 (but downstream from light source 84) can be positioned a series of triggering photodetectors, with photodetector 300 on spacers 302 illustratively representing the series. Alternatively, another type of detector could be used, such as a Coulter counter or Mie scatter sensor.

Within portion 80, fluorescing objects 310, 312, and 314 are being carried through channel 14. As they fluoresce, objects 310, 312, and 314 emanate photons, represented respectively by rays 320, 322, and 324. Quantities read out from a photosensor array in detector 87 can be used to obtain information about objects 310, 312, and 314 even though all three objects are concurrently traveling past the array, as described in co-pending U.S. patent application Ser. No. 11/315,992, entitled "Sensing Photons From Objects in Channels" and incorporated herein by reference in its entirety.

Figure 19:
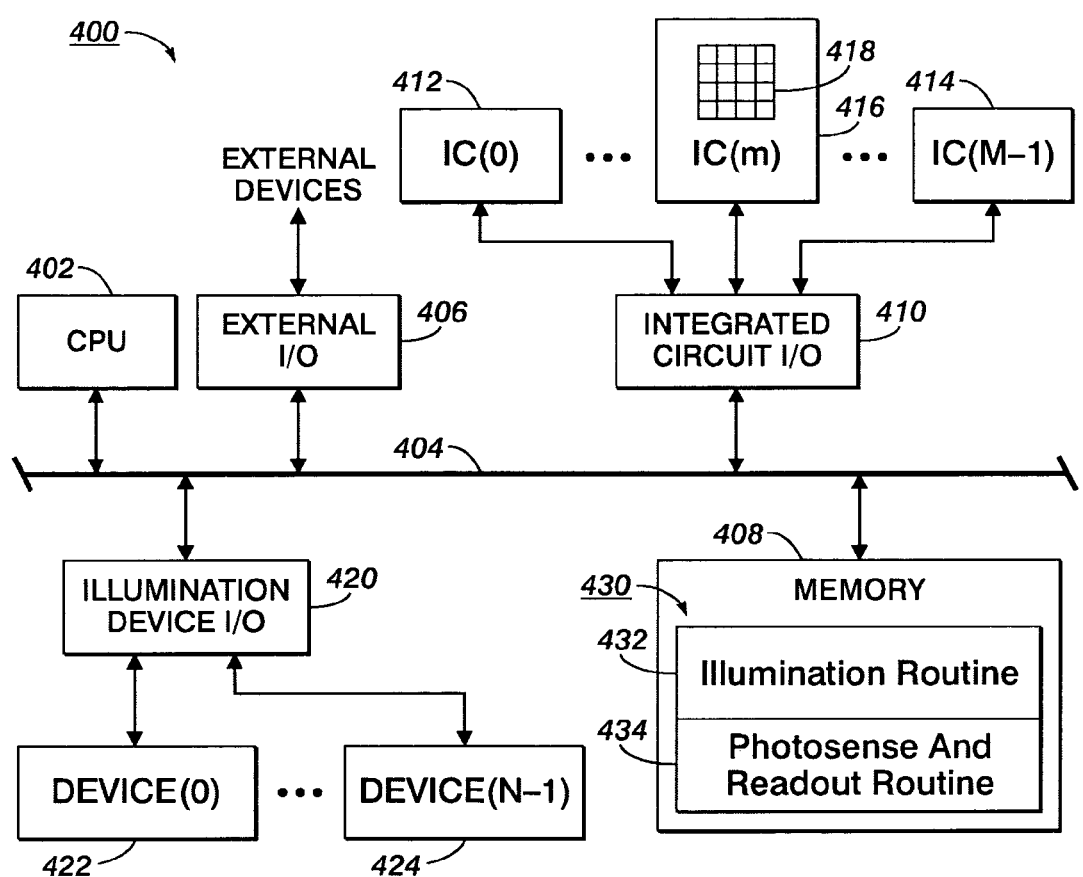
FIG. 19 is a schematic block diagram of a system that can control the analyzer of FIG. 1.

FIG. 19 illustrates system 400, an exemplary system that could be used to operate analyzer 10. Although system 400 illustratively includes central processing unit (CPU) 402 connected to various components through bus 404, a wide variety of other architectures could be employed, including any appropriate combination of hardware and software, as well as specialized hardware components such as application specific integrated circuits (ASICs) for one or more of the illustrated components or in place of a software component executed by CPU 402.

System 400 also includes external input/output (I/O) component 406 and memory 408, both connected to bus 404. External I/O 406 permits CPU 402 to communicate with devices outside of system 400.

Additional components connected to bus 404 are within or connected to analyzer 10. In the illustrated implementation of system 400, IC I/O 410 is a component that permits CPU 402 to communicate with ICs in analyzer 10, such as the various ICs, photo detectors, and other sensing components described above; M ICs are illustrated in FIG. 19 by a series extending from IC(0) 412 to IC (M-1) 414. ICs 412 through 414 illustratively include IC(m) 416 with a photosensor array 418, which includes cells that photosense subranges as described above. Similarly, illumination device I/O 420 is a component permitting CPU 402 to communicate with various illumination devices such as lasers, light emitting diodes, halogen lamps, and so forth; N illumination devices are represented in FIG. 19 by device (0) 422 through device (N-1) 424.

Memory 408 illustratively includes program memory 430, although instructions for execution by CPU 402 could be provided in various other forms of software or hardware, on or off of CPU 402. The routines stored in program memory 430 illustratively include illumination routine 432 and photosense and readout routine 434. In addition, program memory 430 can also store a number of subroutines (not shown) that CPU 402 can call in executing routines 432 and 434.

CPU 402 can, for example, execute illumination routine 432 to communicate with light sources 84 and 244. For example, CPU 402 can receive signals from sensors, perform computations to determine what illumination operations are necessary, and then provide signals to activate light sources 84 and 244. Exemplary operations could include switching a light source on and off for time-gated measurement; switching between different light sources; or adjusting or selecting a coupling angle in response to changing refractive index, such as due to a change in composition of fluid, e.g. salt concentration change. The coupling angle could, for example, be adjusted by a small piezo-motor.

Similarly, CPU 402 can execute photosense and readout routine 434 to obtain information from cells in ICs 412 through 414, which can include, for example, ICs 64, 66, 68, 70, 252, and 290, as described above. For example, CPU 402 can provide signals so that photosensing is performed during an appropriate sensing period, after which signals are received from the cells of an IC by CPU 402. Various techniques that could be used are described in co-pending U.S. patent application Ser. No. 11/315,992, entitled "Sensing Photons from Objects in Channels" and incorporated herein by reference in its entirety.

The implementations of the techniques illustrated in FIGS. 1-19 illustrate examples of a method of sensing photons emanating from a channel portion defined in a fluidity structure. At each position along its length in a longitudinal direction, the channel portion has a cross section in which most of its boundary is surrounded by material with higher refractive index than a fluid in the channel portion would have. With fluid in the channel portion, the method propagates light in the longitudinal direction through the channel portion so that more than approximately 10% of light intensity occurs in the fluid. The method uses a set of cells of a photosensor array on an IC positioned along the channel portion to sense photons that emanate in response to the propagated light.

Implementations of techniques illustrated in FIGS. 1-19 also illustrate examples of apparatus that includes a fluidity structure within which a channel portion as described above is defined. The apparatus also includes an illumination component that provides light that propagates through the channel portion in the longitudinal direction so that more than approximately 10% of light intensity occurs in the fluid. The apparatus also includes an IC with a photosensor array having a set of cells along the channel portion, and the set of cells senses photons that emanate in response to the propagated light.

In specific implementations of FIGS. 1-19, the illumination component includes a source that provides light that enters the channel portion in an oblique direction. The source can provide light through a light-transmissive component along at least part of the channel portion's boundary, or through a light-transmissive portion of an end component at an end of the channel portion. In the latter case, light can enter a projection of the channel portion that contains air through a light-transmissive component, and then pass through the projection of the channel portion to the light-transmissive portion of the end component. The end component can have a convex surface disposed away from the channel portion to focus or collimate light. Or the end component can have an oblique light entry surface disposed away from the channel portion. A system that includes the apparatus can also include a processor connected to receive information from the set of cells.

Implementations of techniques illustrated in FIGS. 9-11 in particular also illustrate examples of apparatus that includes a fluidity structure within which is defined a channel extending in a longitudinal direction. The fluidity structure includes a light-transmissive bounding component between first and second portions of the channel, and also has ports through which fluid can enter and exit the first portion. The bounding component is positioned so that light can enter the second portion at a first oblique angle, pass through the bounding component, and enter the first portion at a second oblique angle.

In specific implementations of FIGS. 9-11, the fluidity structure includes a light-transmissive component along at least part of the channel portion's boundary with an exterior surface substantially parallel to the channel's boundary, and the bounding component is positioned so that light can enter through the exterior surface and exit into the second portion at the first oblique angle. The light entering the first portion can couple to an anti-resonant waveguide mode of the first portion. The bounding component can have a convex surface disposed away from the channel portion to focus or collimate light. Or the bounding component can have an oblique light entry surface disposed away from the channel portion. A system that includes the apparatus can also include an IC including a photosensor array with a set of cells that senses photons emanating in response to light entering the first portion from the bounding component, and also a processor connected to receive information from the set of cells. The IC can be separated from the fluidity structure by a gap so that it does not interfere with propagation of light in the first portion.

Implementations of techniques illustrated in FIGS. 1-19, especially FIG. 14, also illustrate examples of methods of producing an apparatus as described above.

Various of the techniques described above have been successfully implemented or simulated, including the production of a detector that includes a commercially available IC covered with a laterally graded Fabry-Perot cavity filter on a glass slide. Wavelength resolution has been experimentally determined and successfully simulated on a computer. Anti-resonant waveguide techniques have been successfully tested, including the technique illustrated in FIG. 9 as described above.

The exemplary implementations described above are advantageous because they provide various ways of producing enhanced light-target interaction in a channel or channel portion and sensing of photons that emanate as a result. In particular, the exemplary implementations can be used to provide coupling to anti-resonant waveguide modes of a channel or channel portion, including where illumination through end facets is not feasible.

More generally, the exemplary implementations described above are advantageous because they can provide compact, inexpensive components that generally require no additional mechanical or optical parts to perform functions such as spectrometry. For example, a portable, easy-to-use spectrometer could include an analyzer as described above; a portable, compact unit could, for example, be standard equipment for emergency response teams anywhere. The results of photosensing can be read out rapidly and in parallel from a number of ICs, allowing fast data acquisition; as a result, an initial characterization of an object may be used to determine whether to perform more refined or detailed analysis of the object, or to determine which of different types of analysis are performed. A multi-signal approach like this is compatible with reagentless identification, i.e. without specific binding, tagging, labeling, dyes, or stains; also, a wide variety of objects can be identified in a wide variety of fluids, such as various nanoparticles, microorganisms, bioagents, and toxins in various aerosols, water, blood, food, and other specimens.

The implementations generally permit a continuous flow of analytes through an analyzer, allowing real-time analysis, such as in a chemical reactor for real-time feedback, and also allowing the possibility of interactive detection schemes. The use of a variety of compact optical sensing components, as described above, makes it possible to analyze objects without use of reagents, although the techniques described above could be used with reagents for excitation. Because the techniques can use a number of ICs with photosensor arrays, different ICs may address different ranges of photon energies, and a wide range may be addressed by using suitable coating materials on the ICs, possibly ranging from the ultraviolet to the far infrared and even into the terahertz range.

More generally, the implementations described above allow the combination of many different electrical and optical detection schemes on a single platform, in an approach that could be used on a wide variety of platforms. The techniques are particularly advantageous with a microfluidics architecture and an all-aerosol-based system that combines handling and unique identification of analytes on a compact, but extensible, platform.

Spectrometry measurements have a wide variety of applications, including, for example, optical instrumentation, telecommunications, fluorescence devices, process control, optical signal scanning, detection systems for chemical and biological agents, and so forth. An example of a specific application is an in-line detector for manufacturing and functionalizing colloidal particles in an industrial setting. In this application, processes typically are performed in closed systems and the properties of colloidal particles can be assessed only after all processing steps are completed. A small detection platform implemented as described above can be easily built into an on-line detector directly connected to a manufacturing vessel. As a result, small amounts of particles can be analyzed continuously in real time to determine size, chemical composition, and surface conditions. This approach permits instant process adjustments leading to production of materials with consistent properties from run to run. In-line Coulter counters for instant size measurements are already commercially available, but compact detectors as described above can also probe chemical composition using multiple advanced spectroscopic methods, an approach not previously available.

Various specific spectroscopic techniques can be implemented with the techniques described above, including absorption spectroscopy (e.g. gas sensing), fluorescence spectroscopy, and Raman spectroscopy, all of which are discussed above. The techniques spectroscopy, and Raman spectroscopy, all of which are discussed above. The techniques described above, however, are not limited specifically to spectroscopy, but could also be applied in other photosensing situations. Additional description of applications in which photon energy is sensed in combination with relative motion is found in co-pending U.S. patent application Ser. No. 11/315,926, entitled "Sensing Photon Energies of Optical Signals"; and U.S. patent application Ser. No. 11/315,992, entitled "Sensing Photon Energies Emanating From Channels or Moving Objects", both of which are incorporated herein by reference.

Components could have various shapes, dimensions, or other numerical or qualitative characteristics other than those illustrated and described above. For example, in the exemplary implementations described above, fluidity and light-transmissive structures are shown with particular optical properties, but these are merely illustrative.

Some of the above exemplary implementations involve specific materials, such as in fluidity structures, bounding components, end components, photosensor arrays, and light-transmissive structures, but the invention could be implemented with a wide variety of materials and with layered structures with various combinations of sublayers. In particular, light-transmissive components could have any suitable material, and could be produced with any appropriate characteristics. In some of the above-illustrated examples, a convex surface or an oblique light entry surface of a bounding or end component is disposed away from a channel portion, but there are various other possibilities: An oblique surface could be disposed toward the channel portion; both surfaces of the component could be oblique; or, more generally, the component could have any convex, concave, cylindrical, or oblique shape, with a general objective being better control of coupling angle as well as appropriate focusing, collimating, and spreading capabilities.

Some of the above exemplary implementations employ an arrangement of ICs relative to fluidity structures within which fluid moves and carries objects, and a wide variety of such arrangements could be made within the scope of the invention. The invention could also be implemented with any other suitable type of photosensor or other devices that employ illumination of a fluidity structure. Although objects could be photosensed one at a time, the techniques described above also allow concurrent photosensing of multiple objects. In one example, a preliminary inspection of an analyte could be made with an IC with a 400-700 nm laterally varying filter to detect fluorescence or scattering in the 400-700 nm range, after which a more refined inspection could be made with another IC, such as to perform Raman spectroscopy in the range of 100 $cm^{-1}$ to a few 1000 $cm^{-1}$. Rather than using separate ICs, different rows of a single two-dimensional photosensor array on an IC could be differently coated to photosense in different ranges.

The above exemplary implementations generally employ fluidity structures and enhanced light-target interaction to obtain fluorescence or scattering. In general, however, the techniques described above could also be used for self-emitting or auto-fluorescing objects such as particles. Furthermore, various types of fluorescence, photo-luminescence, chemo-fluorescence, inelastic scattering, and so forth could be employed.

The technique of anti-resonant waveguiding, described above, is only one of many illumination techniques that could be used for enhanced light-target interaction, and any such excitation technique could be applied continuously or intermittently along a path. Various parameters could be adjusted to obtain anti-resonant waveguiding, including the shape of quartz or glass surrounding the channel; a thinner structure is generally better, with a surface parallel to the channel generally being required.

The exemplary implementation in FIG. 19 employs a CPU, which could be a microprocessor or any other appropriate component. In general, routines as described above in relation to FIG. 19 could be done either on the same IC as a photosensor array, on other components, or on a combination of the two, with any appropriate combination of software or hardware.

The above exemplary implementations generally involve production and use of photosensor arrays, ICs, light-transmissive structures, fluidity structures, illumination components, optical components, and analyzers following particular operations, but different operations could be performed, the order of the operations could be modified, and additional operations could be added within the scope of the invention.

While the invention has been described in conjunction with specific exemplary implementations, it is evident to those skilled in the art that many alternatives, modifications, and variations will be apparent in light of the foregoing description. Accordingly, the invention is intended to embrace all other such alternatives, modifications, and variations that fall within the spirit and scope of the appended claims.

The invention claimed is:

1. A method of sensing photons emanating from a channel portion defined in a fluidic structure, the channel portion extending a length in a longitudinal direction and having, at each position along its length, a respective cross section; in each position's cross section, the channel portion having a boundary along most of which it is surrounded by material with higher refractive index than a fluid in the channel portion would have; the fluidic structure including an end component at an end of the channel portion, the end component including a light-transmissive portion; the fluidic structure further including a light-transmissive component that extends in the longitudinal direction along at least part of the channel portion's boundary and beyond the end component to a projection of the channel portion; the method comprising:

with fluid in the channel portion, propagating light in the longitudinal direction through the channel portion so that, in cross sections along a part of the length, more than approximately 10% of light intensity from the propagated light occurs in the fluid; the act of propagating light including:

providing light from a source outside the channel portion through the light-transmissive component beyond the end component, through the projection of the channel portion, and through the light-transmissive portion of the end component; the light from the source entering the channel portion in a direction oblique to the longitudinal direction; and photosensing photons emanating from the channel portion in response to the propagated light.

2. The method of claim 1 in which, in the cross sections along the part of the length, approximately 90% of light intensity from the propagated light occurs in the fluid.

3. The method of claim 1 in which the light-transmissive component has an approximately planar light entry surface that is oblique to the longitudinal direction; the light from the source being provided at approximately normal through the light entry surface.

4. The method of claim 1 in which the projection of the channel portion contains air, gas, or vacuum.

5. The method of claim 1 in which the act of providing light further comprises:

coupling the light from the source to an anti-resonant waveguide mode of the channel portion.

6. The method of claim 1 in which the act of photosensing photons further comprises:

using a set of cells of a photosensor array on an IC positioned along the channel portion to sense photons emanating from the channel portion in response to the propagated light.

7. Apparatus comprising:

a fluidic structure;

defined within the fluidic structure, a channel portion that can contain fluid; the channel portion extending a length in a longitudinal direction and having, in each position along its length, a respective cross section; in each position's cross section, the channel portion having a boundary along most of which it is surrounded by material with higher refractive index than the fluid;

an end component in the fluidic structure at an end of the channel portion, the end component including a light-transmissive portion;

included in the fluidic structure, a light-transmissive component that extends in the longitudinal direction along at least part of the channel portion's boundary and beyond the end component to a projection of the channel portion; and an illumination component that provides light that propagates through the channel portion in the longitudinal direction; in cross sections along a part of the length, more than approximately 10% of light intensity from the propagating light occurring in the fluid in the channel portion; the illumination component including a source that provides light from outside the channel portion; the source providing light through the light-transmissive component beyond the end component, through the projection of the channel portion, and through the light-transmissive portion of the end component; the light from the source entering the channel portion in a direction oblique to the longitudinal direction.

8. The apparatus of claim 7 in which the light-transmissive component has an approximately planar exterior surface that is neither parallel nor perpendicular to the longitudinal direction; the source providing light at approximately normal through the exterior surface.

9. The apparatus of claim 7 in which the light-transmissive component includes at least one of polydimethylsiloxane, polymer, glass, and quartz.

10. The apparatus of claim 7 in which the projection of the channel portion contains air, gas, or vacuum.

11. The apparatus of claim 10 in which the fluidic structure further includes an outer component in the projection of the channel and outward from the end component, the air, gas, or vacuum being contained between the outer and end components.

12. The apparatus of claim 7 in which the end component has a convex surface; the convex surface focusing or collimating the light from the source.

13. The apparatus of claim 7 in which the end component has an oblique light entry surface.

14. The apparatus of claim 7 in which the illumination component includes at least one of a laser and a light-emitting diode.

15. The apparatus of claim 7, further comprising:

an IC that includes a photosensor array with a set of cells along the channel portion; the set of cells sensing photons emanating from the channel portion in response to the propagating light.

16. A system that comprises the apparatus of claim 15, the system further comprising:

a processor connected to receive information from the set of cells.

17. Apparatus comprising:

a fluidic structure; and defined within the fluidic structure, a channel extending in a longitudinal direction; the fluidic structure including a light-transmissive bounding component between first and second portions of the channel; the fluidic structure further having defined therein at least two ports through which fluid can enter and exit the first portion;

the bounding component being positioned so that light can enter the second portion at a first angle oblique to the longitudinal direction, pass through the bounding component, and enter the first portion of the channel at a second angle oblique to the longitudinal direction.

18. The apparatus of claim 17 in which the second angle is approximately 2° or less.

19. The apparatus of claim 17 in which the fluidic structure further comprises a light-transmissive component that extends in the longitudinal direction along at least part of the second portion of the channel and has an exterior surface substantially parallel to the channel's boundary; the bounding component being positioned so that light can enter through the exterior surface of the light-transmissive component and exit into the second portion at the first angle.

20. The apparatus of claim 19 in which the light-transmissive component has entry and exit ports defined therein through which fluid can enter and exit the first portion of the channel.

21. The apparatus of claim 17 in which light entering the first portion of the channel at the second angle couples to an anti-resonant waveguide mode of the first portion.

22. The apparatus of claim 17 in which the bounding component comprises at least one of gel, polydimethylsiloxane, polymer, photoresist, SU-8, glass, and quartz.

23. The apparatus of claim 17 in which the bounding component has a convex surface disposed away from the first portion of the channel; the convex surface focusing or collimating the light from the second portion.

24. The apparatus of claim 17 in which the bounding component has an oblique light entry surface.

25. The apparatus of claim 17 in which the fluidic structure further includes an outer component in the second portion of the channel and outward from the bounding component, the second portion containing air, gas, or vacuum between the outer component and the bounding component.

26. A system that comprises the apparatus of claim 17, the system further comprising:
an IC that includes a photosensor array with a set of cells along the first portion of the channel, the set of cells sensing photons emanating from the first portion of the channel in response to the light entering from the bounding component; and
a processor connected to receive information from the set of cells.

27. The system of claim 26 in which the IC is separated from the fluidic structure by a gap so that the IC does not interfere with propagation of light in the first portion of the channel.

28. A method of producing an apparatus as in claim 17, the method comprising:
positioning the bounding component within the channel so that light can enter the second portion of the channel at a first angle oblique to the longitudinal direction, pass through the bounding component, and enter the first portion of the channel at a second angle oblique to the longitudinal direction.

29. Apparatus comprising:
a fluidic structure;
defined within the fluidic structure, a channel portion that can contain fluid; the channel portion extending a length in a longitudinal direction and having, in each position along its length, a respective cross section; in each position's cross section, the channel portion having a boundary along most of which it is surrounded by material with higher refractive index than the fluid;
an illumination component that provides light that propagates through the channel portion in the longitudinal direction; in cross sections along a part of the length, more than approximately 10% of light intensity from the propagating light occurring in the fluid in the channel portion;
one or more spacers on the fluidic structure outside the channel portion; and
a sensing component with an IC that includes a photosensor array with a set of cells along the channel portion; the set of cells sensing photons emanating from the channel portion in response to the propagating light; the sensing component being supported on a set of one or more of the spacers with sufficient separation between the sensing component and the fluidic structure that the sensing component does not interfere with propagation of light in the channel portion.

30. The apparatus of claim 29 in which the illumination component includes a source that provides light from outside the channel portion; the light from the source entering the channel portion in a direction oblique to the longitudinal direction.

31. The apparatus of claim 30 in which the fluidic structure comprises:
a light-transmissive component along at least part of the channel portion's boundary, the source providing light through the light-transmissive component.

32. The apparatus of claim 30 in which the fluidic structure includes an end component at an end of the channel portion, the end component including a light-transmissive portion; the source providing light through the light-transmissive portion.

33. The apparatus of claim 29 in which at least one of the spacers is shaped and positioned to absorb light emanating from the channel portion.

34. Apparatus comprising:
a fluidic structure; and
defined within the fluidic structure, a channel extending in a longitudinal direction between first and second ends at both of which the channel is enclosed; the fluidic structure including, between the first and second ends, a light-transmissive bounding component separating first and second portions of the channel; the fluidic structure further having defined therein at least two ports between the bounding component and the first end through which fluid can enter and exit the first portion; the second portion containing air, gas, or vacuum between the bounding component and the second end;
the bounding component being positioned so that light propagating through the second portion at a first angle oblique to the longitudinal direction can pass through the bounding component and enter the first portion of the channel at a second angle oblique to the longitudinal direction; the second angle being smaller than the first angle,
an IC that includes a photosensor array with a set of cells along the channel portion; the set of cells sensing photons emanating from the channel portion in response to the propagating light.

35. The apparatus of claim 34 in which the fluidic structure further comprises a light-transmissive component that extends in the longitudinal direction along at least part of the second portion of the channel and has an exterior surface substantially parallel to the channels boundary; the bounding component being positioned so that light can enter through the exterior surface of the light-transmissive component and exit into the second portion at the first angle.

* * * * *